United States Patent
Shin

(10) Patent No.: US 11,972,603 B2
(45) Date of Patent: Apr. 30, 2024

(54) IMAGE VERIFICATION METHOD, DIAGNOSTIC SYSTEM PERFORMING SAME, AND COMPUTER-READABLE RECORDING MEDIUM HAVING THE METHOD RECORDED THEREON

(71) Applicant: THYROSCOPE INC., Ulsan (KR)

(72) Inventor: Kyubo Shin, Ulsan (KR)

(73) Assignee: THYROSCOPE INC., Ulsan (KR)

( * ) Notice: Subject to any disclaimer, the term of this patent is extended or adjusted under 35 U.S.C. 154(b) by 0 days.

(21) Appl. No.: 18/130,464

(22) Filed: Apr. 4, 2023

(65) Prior Publication Data
US 2023/0298328 A1    Sep. 21, 2023

Related U.S. Application Data

(63) Continuation of application No. PCT/KR2023/003497, filed on Mar. 16, 2023.

(30) Foreign Application Priority Data

Mar. 21, 2022    (KR) .................. 10-2022-0034726

(51) Int. Cl.
*G06V 10/776*    (2022.01)
*A61B 3/14*    (2006.01)
(Continued)

(52) U.S. Cl.
CPC .............. *G06V 10/776* (2022.01); *A61B 3/14* (2013.01); *A61B 5/4227* (2013.01);
(Continued)

(58) Field of Classification Search
CPC .............. G06V 10/776; G06V 40/193; G06V 2201/03; G06T 7/73; G06T 7/0014;
(Continued)

(56) References Cited

U.S. PATENT DOCUMENTS

2020/0066394 A1* 2/2020 Toyoda ................. G16H 10/60
2022/0237898 A1* 7/2022 Uehara ................. G06V 10/776
2022/0313077 A1* 10/2022 Singh ................... A61B 3/0025

FOREIGN PATENT DOCUMENTS

KR    1020100106965 A    10/2010
KR    1020140088434 A    7/2014
(Continued)

OTHER PUBLICATIONS

Office Action of KR Application No. 10-2022-0034726 dated May 17, 2022.
(Continued)

*Primary Examiner* — Vu Le
*Assistant Examiner* — Winta Gebreslassie
(74) *Attorney, Agent, or Firm* — Dinsmore & Shohl LLP; Yongsok Choi, Esq.

(57) ABSTRACT

Provided is a diagnostic system including: a user terminal configured to take an image; and a server configured to obtain diagnosis assistance information on the basis of the image. The user terminal is configured to obtain a first photographing parameter, determine whether a pre-stored condition is satisfied, and transmit the first photographing parameter and a captured image to the server when it is determined that the pre-stored condition is satisfied. The server is configured to obtain a first verification parameter, determine whether to use the captured image as a diagnostic image which includes comparing the first verification parameter with the first photographing parameter, and obtain the diagnosis assistance information by using the diagnostic image when it is determined to use the captured image as the diagnostic image.

20 Claims, 16 Drawing Sheets

(51) Int. Cl.
  *A61B 5/00* (2006.01)
  *G06T 7/00* (2017.01)
  *G06T 7/33* (2017.01)
  *G06T 7/73* (2017.01)
  *G06V 40/18* (2022.01)
  *G16H 30/40* (2018.01)
  *H04N 7/18* (2006.01)

(52) U.S. Cl.
  CPC .............. *G06T 7/0014* (2013.01); *G06T 7/73* (2017.01); *G06V 40/193* (2022.01); *G16H 30/40* (2018.01); *H04N 7/183* (2013.01); *G06T 2207/20021* (2013.01); *G06T 2207/20081* (2013.01); *G06T 2207/30041* (2013.01); *G06V 2201/03* (2022.01)

(58) Field of Classification Search
  CPC . G06T 2207/20021; G06T 2207/20081; G06T 2207/30041; G06T 2207/10004; G06T 7/70; G16H 30/40; G16H 30/20; A61B 3/14; A61B 5/4227; H04N 7/183
  See application file for complete search history.

(56) References Cited

FOREIGN PATENT DOCUMENTS

| KR | 1020200044209 A | 4/2020 |
| KR | 1020200105079 A | 9/2020 |
| KR | 1020210110541 A | 9/2021 |
| KR | 102459723 B1 | 10/2022 |

OTHER PUBLICATIONS

Notice of Allowance of KR Application No. 10-2022-0034726 dated Jul. 28, 2022.
International Search Report of PCT/KR2023/003497 dated Jun. 19, 2023.
Written Opinion of the International Searching Authority of PCT/KR2023/003497 dated Jun. 19, 2023.

* cited by examiner

FIG. 10

|  | IF1 | IF2 | IF3 | IF4 | IF5 | IF6 | IF7 | IF8 | IF9 | IF10 |
|---|---|---|---|---|---|---|---|---|---|---|
| S131 | O | O | X | O | X | X | X | O | O |  |
| S132 | X | X | X | O | O | O | O | O | O |  |
| ⋮ |  |  |  |  |  |  |  |  |  |  |
| S133 | X |  |  | X |  |  | O |  |  |  |

IMAGE VERIFICATION METHOD, DIAGNOSTIC SYSTEM PERFORMING SAME, AND COMPUTER-READABLE RECORDING MEDIUM HAVING THE METHOD RECORDED THEREON

CROSS-REFERENCE TO RELATED APPLICATIONS

This application is a continuation of International Application No. PCT/KR2023/003497 filed on Mar. 16, 2023, which claims priority to Korean Patent Application No. 10-2022-0034726 filed on Mar. 21, 2022, the entire contents of which are herein incorporated by reference.

TECHNICAL FIELD

An embodiment relates to an image verification method used for disease diagnosis.

An embodiment relates to a diagnostic system for performing the image verification method used for disease diagnosis.

An embodiment relates to a computer-readable recording medium on which the image verification method used for disease diagnosis is recorded.

BACKGROUND ART

With the active development of software for diagnosing cancers by analyzing images or diagnosing specific diseases early by analyzing images, the definition of medical devices has been extended to the software of diagnostic devices for analyzing images to obtain information on disease beyond classical surgical devices, X-ray imaging devices, etc.

If even software falls under a diagnostic device for analyzing human health information, approval according to each country's regulations is essential for the realization and distribution of software. Accordingly, the accuracy of the software and the consistency of results should be generally verified, so improving accuracy is of great significance in the market of medial devices in the form of software.

Therefore, an image acquisition method having consistency that does not degrade the accuracy of a medical device needs to be devised in the software field of providing health information through image analysis.

The foregoing is intended merely to aid in the understanding of the background of the present disclosure, and is not intended to mean that the present disclosure falls within the purview of the related art that is already known to those skilled in the art.

SUMMARY

Technical Problem

An embodiment provides a method of obtaining a diagnostic image used for diagnosis.

An embodiment provides an image verification method of verifying an image to use an appropriate image as a diagnostic image.

Technical Solution

According to an embodiment of the present application, there is provided a diagnostic system including: a user terminal configured to take an image; and a server configured to obtain diagnosis assistance information on the basis of the image, wherein the user terminal is configured to obtain a first photographing parameter including information related to at least one of a detected position of a diagnosis object and whether the diagnosis object is detected by analyzing a first image with a first image analysis algorithm, determine whether a pre-stored condition is satisfied which includes the first photographing parameter satisfies a first condition, and transmit the first photographing parameter and a captured image to the server when it is determined that the pre-stored condition is satisfied, the server is configured to obtain a first verification parameter including information related to at least one of a detected position of the diagnosis object and whether the diagnosis object is detected by analyzing the captured image with a second image analysis algorithm, determine whether to use the captured image as a diagnostic image which includes comparing the first verification parameter with the first photographing parameter, and obtain the diagnosis assistance information by using the diagnostic image when it is determined to use the captured image as the diagnostic image, the first image analysis algorithm and the second image analysis algorithm are different algorithms, and the diagnosis object is a body part associated with a target disease for which the diagnosis assistance information is obtained.

According to an embodiment of the present application, there is provided a diagnostic image verification method including: obtaining a first image; obtaining a first photographing parameter including information related to at least one of a detected position of a diagnosis object and whether the diagnosis object is detected by analyzing the first image with a first image analysis algorithm; determining whether a pre-stored condition is satisfied which includes the first photographing parameter satisfies a first condition; storing the first photographing parameter and a captured image when it is determined that the pre-stored condition is satisfied; obtaining a first verification parameter including information related to at least one of a detected position of the diagnosis object and whether the diagnosis object is detected by analyzing the captured image with a second image analysis algorithm; determining whether to use the captured image as a diagnostic image which comprises comparing the first verification parameter with the first photographing parameter; and obtaining diagnosis assistance information by using the diagnostic image when it is determined to use the captured image as the diagnostic image, wherein the first image analysis algorithm and the second image analysis algorithm are different algorithms, and the diagnosis object is a body part associated with a target disease for which the diagnosis assistance information is obtained.

According to an embodiment of the present application, there is provided a computer-readable recording medium having a program recorded thereon, the program for performing the following: obtaining a first image; obtaining a first photographing parameter including information related to at least one of a detected position of a diagnosis object and whether the diagnosis object is detected by analyzing the first image with a first image analysis algorithm; determining whether a pre-stored condition is satisfied which includes the first photographing parameter satisfies a first condition; storing the first photographing parameter and a captured image when it is determined that the pre-stored condition is satisfied; obtaining a first verification parameter including information related to at least one of a detected position of the diagnosis object and whether the diagnosis object is detected by analyzing the captured image with a second image analysis algorithm; determining whether to use the captured image as a diagnostic image which comprises comparing the first verification parameter with the first photographing parameter; and obtaining diagnosis assistance information by using the diagnostic image when it is determined to use the captured image as the diagnostic image, wherein, the first image analysis algorithm and the second image analysis algorithm are different algorithms, and the diagnosis object is a body part associated with a target disease for which the diagnosis assistance information is obtained.

Advantageous Effects

According to the embodiment, provided is an improved method of obtaining a diagnostic image to ensure the accuracy of a diagnostic device and enable the approval and distribution of a product.

According to the embodiment, provided is the image verification method capable of obtaining an accurate image while maintaining the amount of operation of the image analysis method of the photographing device to enable real-time photographing.

The present application is not limited to the above-mentioned effects. From the present specification and the accompanying drawings, an effect not mentioned above would be understandable to a person of ordinary skill in the art to which the present application pertains.

DESCRIPTION OF DRAWINGS

The above and other objectives, features, and other advantages of the present disclosure will be more clearly understood from the following detailed description when taken in conjunction with the accompanying drawings, in which:

FIGS. 8, 9 and 10 are diagrams specifically illustrating an evaluation target image, the frequency of evaluations of photographing parameters, and a stored captured image according to the speed of determining whether a condition corresponding to each photographing parameter is satisfied;

DETAILED DESCRIPTION

Figure 1:
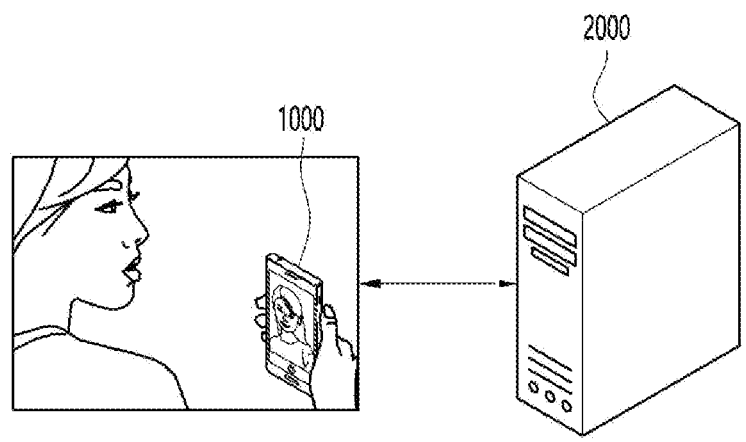
FIG. 1 is a diagram illustrating a configuration of a diagnostic system according to an embodiment of the present application.

Hereinafter, embodiments of the present specification will be described in detail with reference to the accompanying drawings such that the present application can be easily embodied by those skilled in the art to which the present application belongs. In addition, various modifications may be made to the present application, and various embodiments of the present application may be practiced. Therefore, specific embodiments will be described in detail below with reference to the accompanying drawings. The technical idea disclosed in the present specification is not limited to the accompanying drawings or the described embodiments, and the exemplary embodiments can be construed as including all modifications, equivalents, or substitutes in a technical concept and a technical scope of the present application.

Throughout the specification, the same reference numerals denote the same elements in principle. In addition, elements having the same function within the same scope illustrated in the drawings of the embodiments are described using the same reference numerals, and a redundant description will be omitted.

In describing the embodiments disclosed in the present specification, a detailed description of a well-known technology relating to the present specification is omitted when determined as obfuscating the gist of the embodiments disclosed in the present specification. In addition, throughout the present specification, the terms first, second, and so on are used only to distinguish from one element to another.

In addition, the terms "module" and "part" that are used to name an element in the description below are used considering only the ease with which the present specification is written. The terms are not intended as having different special meanings or functions and thus may be used individually or interchangeably.

In the following embodiments, an expression used in the singular encompasses the expression of the plural, unless it has a clearly different meaning in the context.

In the following embodiments, it is to be understood that terms such as "including", "having", etc. are intended to indicate the existence of features or elements disclosed in the specification, and are not intended to preclude the possibility that one or more other features or elements may be added.

Sizes of elements in the drawings may be exaggerated or reduced for convenience of description. For example, any size and thickness of each element shown in the drawings are shown for convenience of description.

In a case in which a particular embodiment is realized otherwise, a method to be described below may be performed out of the order described. For example, two operations described in succession may be performed substantially simultaneously, or may be performed in an order opposite to the order described.

According to an embodiment of the present application, there is provided a diagnostic system including: a user terminal configured to take an image; and a server configured to obtain diagnosis assistance information on the basis of the image, wherein the user terminal is configured to obtain a first photographing parameter including information related to at least one of a detected position of a diagnosis object and whether the diagnosis object is detected by analyzing a first image with a first image analysis algorithm, determine whether a pre-stored condition is satisfied which includes the first photographing parameter satisfies a first condition, and transmit the first photographing parameter and a captured image to the server when it is determined that the pre-stored condition is satisfied, wherein the server is configured to obtain a first verification parameter including information related to at least one of a detected position of the diagnosis object and whether the diagnosis object is detected by analyzing the captured image with a second image analysis algorithm, determine whether to use the captured image as a diagnostic image which includes comparing the first verification parameter with the first photographing parameter, and obtain the diagnosis assistance information by using the diagnostic image when it is determined to use the captured image as the diagnostic image, wherein the first image analysis algorithm and the second image analysis algorithm are different algorithms, and the diagnosis object is a body part associated with a target disease for which the diagnosis assistance information is obtained.

In the diagnostic system, the first photographing parameter may include information on the detected position of the diagnosis object in the first image, and the user terminal may be configured to determine whether the pre-stored condition is satisfied by comparing the first photographing parameter with a pre-stored diagnosis object area.

In the diagnostic system, the first image analysis algorithm may be a first landmark detection algorithm, the target disease may be thyroid eye disease, the diagnosis object may be an eye, and the first photographing parameter may be a landmark of the eye.

In the diagnostic system, the first verification parameter may include information on the detected position of the diagnosis object in the captured image.

In the diagnostic system, the second image analysis algorithm may be a second landmark detection algorithm, the target disease may be thyroid eye disease, the diagnosis object may be an eye, and the first verification parameter may be a landmark of the eye.

In the diagnostic system, the second image analysis algorithm may be an image segmentation algorithm, the target disease may be thyroid eye disease, the diagnosis object may be an eye, and the first verification parameter may be an iris area.

In the diagnostic system, the user terminal may be configured to obtain the images according to a preset frame rate, analyze at least a part of the obtained images with the first image analysis algorithm, store one of the obtained images as the captured image, and transmit the captured image to the server.

In the diagnostic system, the user terminal may be configured to, when it is determined that the first photographing parameter for the first image does not satisfy the first condition, analyze a second image with the first image analysis algorithm, wherein the second image is obtained after it is determined that the first photographing parameter for the first image does not satisfy the first condition.

In the diagnostic system, the user terminal may be configured to, when it is determined that the first photographing parameter for the first image satisfies the first condition, transmit a second image as the captured image to the sever, wherein the second image is obtained after it is determined that the first photographing parameter for the first image satisfies the first condition.

In the diagnostic system, the first image analysis algorithm may have a smaller amount of operation than the second image analysis algorithm to have an advantage of real-time processing.

In the diagnostic system, the user terminal may be configured to obtain a second photographing parameter for the first image, and the pre-stored condition further includes the second photographing parameter satisfies a second condition.

In the diagnostic system, with respect to the user terminal, a period of obtaining the first photographing parameter and a period of obtaining the second photographing parameter may be different from each other.

In the diagnostic system, the user terminal may be configured to obtain a second to an N-th photographing parameter for the first image, and the pre-stored condition further includes at least some of the second to the N-th photographing parameter satisfy a corresponding second to an N-th condition, respectively, wherein the N may be a natural number equal to or greater than 2.

In the diagnostic system, the server may be configured to obtain a second to an M-th verification parameter for the captured image, and determine whether to use the captured image as the diagnostic image further includes determining whether the second to the M-th verification parameter are satisfied, wherein the M may be a natural number equal to or greater than 2.

In the diagnostic system, the server may be configured to obtain the diagnosis assistance information by using the diagnostic image and a diagnostic model, and the diagnostic model may be trained using images including the diagnosis object, and information on whether the target disease has occurred.

According to an embodiment of the present application, there is provided a diagnostic image verification method including: obtaining a first image; obtaining a first photographing parameter including information related to at least one of a detected position of a diagnosis object and whether the diagnosis object is detected by analyzing the first image with a first image analysis algorithm; determining whether a pre-stored condition is satisfied which includes the first photographing parameter satisfies a first condition; storing the first photographing parameter and a captured image when it is determined that the pre-stored condition is satisfied; obtaining a first verification parameter including information related to at least one of a detected position of the diagnosis object and whether the diagnosis object is detected by analyzing the captured image with a second image analysis algorithm; determining whether to use the captured image as a diagnostic image which comprises comparing the first verification parameter with the first photographing parameter; and obtaining diagnosis assistance information by using the diagnostic image when it is determined to use the captured image as the diagnostic image, wherein the first image analysis algorithm and the second image analysis algorithm are different algorithms, and the diagnosis object is a body part associated with a target disease for which the diagnosis assistance information is obtained.

In the diagnostic image verification method, the first photographing parameter may include information on the detected position of the diagnosis object in the first image, and the determining whether the pre-stored condition is satisfied may include comparing the first photographing parameter with a pre-stored diagnosis object area.

In the diagnostic image verification method, the first image analysis algorithm may be a first landmark detection algorithm, the target disease may be thyroid eye disease, the diagnosis object may be an eye, and the first photographing parameter may be a landmark of the eye.

In the diagnostic image verification method, the first verification parameter may include information on the detected position of the diagnosis object in the captured image.

In the diagnostic image verification method, the second image analysis algorithm may be a second landmark detection algorithm, the target disease may be thyroid eye disease, the diagnosis object may be an eye, and the first verification parameter may be a landmark of the eye.

In the diagnostic image verification method, the second image analysis algorithm may be an image segmentation algorithm, the target disease may be thyroid eye disease, the diagnosis object may be an eye, and the first verification parameter may be an iris area.

In the diagnostic image verification method may include obtaining images according to a preset frame rate, analyzing at least a part of the obtained images with the first image analysis algorithm, and storing one of the obtained images as the captured image when it is determined that the pre-stored condition is satisfied for at least the part of the obtained images.

In the diagnostic image verification method may include obtaining a second image when it is determined that the first photographing parameter for the first image does not satisfy the first condition, obtaining a first photographing parameter for the second image by analyzing the second image with the first analysis algorithm, and determining whether the first photographing parameter for the second image satisfies the first condition to determine whether the pre-stored condition is satisfied.

In the diagnostic image verification method may include, obtaining a second image when it is determined that the first photographing parameter for the first image satisfies the first condition, and storing the second image as the captured image.

In the diagnostic image verification method, the first image analysis algorithm may have a smaller amount of operation than the second image analysis algorithm to have an advantage of real-time processing.

The diagnostic image verification method may further include, obtaining a second photographing parameter for the first image, and wherein the pre-stored condition further comprises the second photographing parameter satisfies a second condition.

In the diagnostic image verification method, a period of obtaining the first photographing parameter and a period of obtaining the second photographing parameter may be different from each other.

In the diagnostic image verification method may further include, obtaining a second to an N-th photographing parameter for the first image, wherein the N is a natural number equal to or greater than 2, wherein the pre-stored condition further includes at least some of the second to the N-th photographing parameters satisfy a corresponding second to an N-th condition, respectively.

The diagnostic image verification method may further include obtaining a second to an M-th verification parameter for the captured image, wherein the M may be a natural number equal to or greater than 2, wherein the determining of whether to use the captured image may further include determining whether the second to the M-th verification parameter are satisfied.

In the diagnostic image verification method, the obtaining of the diagnosis assistance information by using the diagnostic image when it is determined to use the captured image as the diagnostic image may include obtaining the diagnosis assistance information by using the diagnostic image and a diagnostic model, and the diagnostic model may be trained using images including the diagnosis object, and information on whether the target disease has occurred.

According to an embodiment of the present application, there is provided a computer-readable recording medium having a program recorded thereon, the program for performing the following: obtaining a first image; obtaining a first photographing parameter including information related to at least one of a detected position of a diagnosis object and whether the diagnosis object is detected by analyzing the first image with a first image analysis algorithm; determining whether a pre-stored condition is satisfied which includes the first photographing parameter satisfies a first condition; storing the first photographing parameter and when it is determined that the pre-stored condition is satisfied; obtaining a first verification parameter including information related to at least one of a detected position of the diagnosis object and whether the diagnosis object is detected by analyzing the captured image with a second image analysis algorithm; determining whether to use the captured image as a diagnostic image which comprises comparing the first verification parameter with the first photographing parameter; and obtaining diagnosis assistance information by using the diagnostic image when it is determined to use the captured image as the diagnostic image, wherein the first image analysis algorithm and the second image analysis algorithm are different algorithms, and the diagnosis object is a body part associated with a target disease for which the diagnosis assistance information is obtained.

In the present specification, described will be a diagnostic image verification method, a server using the same, and a diagnostic system that may be used to manufacture a product capable of deriving a diagnosis result with high accuracy, to ensure clinical data required to follow each country's approval procedure for the product, and/or to provide the approved product to a consumer, in realizing a diagnostic device (including software) or system using an image.

FIG. 1 is a diagram illustrating a configuration of a diagnostic system according to an embodiment of the present application.

As shown in FIG. 1, the diagnostic system may include a photographing device 1000 and a server 2000, and the photographing device 1000 and the server 2000 may be connected to each other over a network for data exchange.

The photographing device 1000 may perform a function of taking images. For example, the photographing device 1000 may evaluate whether an image satisfies photographing conditions. The photographing device 1000 may obtain an image, and when determining that the obtained image satisfies the photographing conditions, the photographing device 1000 stores a captured image. A process in which the photographing device 1000 determines whether the image satisfies the photographing conditions will be described in detail later.

The photographing device 1000 is an electronic device capable of taking images. Examples of the photographing device 1000 may include a mobile phone, a smartphone, a tablet PC, a laptop, a portable camera with communication function, and/or a stand-alone camera, but are not limited thereto.

The photographing device 1000 may communicate with the server 2000, and may transmit the captured image to the server 2000.

The server 2000 may perform a function of verifying images. For example, the server 2000 may evaluate whether the received image satisfies verification conditions, and may store the received image as a diagnostic image. A process in which the server 2000 determines whether the image satisfies the verification conditions will be described in detail later.

When the photographing device 1000 determines whether a target image satisfies the photographing conditions, it may be evaluated whether the condition for at least one photographing parameter is satisfied, and the at least one photographing parameter may be related to a diagnosis object DO. According to an embodiment, the photographing parameter may include information related to a detected position of the diagnosis object DO and/or whether the diagnosis object DO is detected.

When the server 2000 determines whether the captured image satisfies the verification conditions, it may be evaluated whether the condition for at least one verification parameter is satisfied, and the at least one verification parameter may be related to a diagnosis object DO. According to an embodiment, the verification parameter may include information related to a detected position of the diagnosis object DO and/or whether the diagnosis object DO is detected.

The diagnosis object DO described in the present specification may mean an object (target object) related to a target disease to be diagnosed. For example, the diagnosis object DO may mean a body part related to the target disease.

According to an embodiment of the present application, the diagnosis object DO evaluated with the verification parameters and the diagnosis object DO evaluated with the photographing parameters may be the same. Alternatively, the diagnosis object DO evaluated with the verification parameters may be included in the diagnosis object DO evaluated with the photographing parameters, or vise versa.

The server 2000 may use the image stored as the diagnostic image, to obtain information on the target disease. Herein, the information on the target disease may be information for assisting in disease diagnosis. For example, the information on the target disease may be a probability that a photographed person in the image has the target disease, or a probability that the person has one or more other diseases known to be related to the target disease.

Figure 2A:
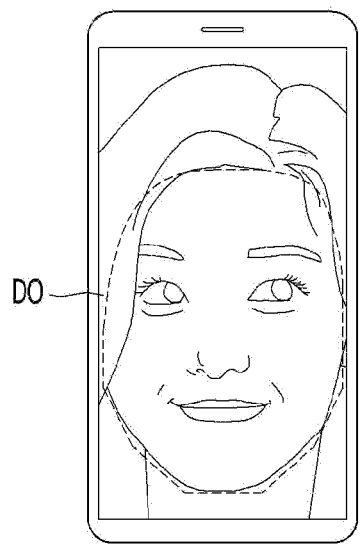
FIGS. 2A, 2B and 2C are diagrams illustrating examples of a diagnosis object DO described in the present application.
Figure 2B:
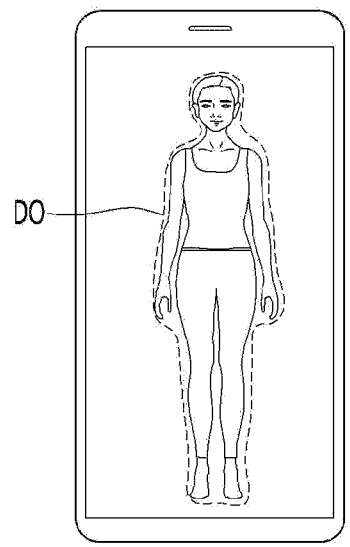
Figure 2C:
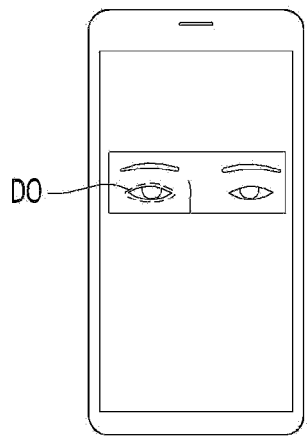

FIGS. 2A, 2B and 2C are diagrams illustrating examples of a diagnosis object DO described in the present application.

According to an embodiment, an image used in a diagnostic device for analyzing phenotypic abnormality by analyzing a facial image may be verified using a diagnostic image verification method described in the present application. A diagnosis object DO for phenotypic abnormality may be a "face" (see FIG. 2A).

According to another embodiment, an image used in the diagnostic device for analyzing body balance by analyzing an entire body image may be verified using the diagnostic image verification method described in the present application. A diagnosis object DO for body imbalance may be the "entire body" (see FIG. 2B).

According to still another embodiment, an image used in the diagnostic device for analyzing thyroid eye disease by analyzing an eye image may be verified using the diagnostic image verification method described in the present application. A diagnosis object DO for thyroid eye disease may be "eyes" (see FIG. 2C).

A diagnosis object DO related to a target disease may mean an object (for example, a body part to be examined for diagnosis) widely known to be used in diagnosing the target disease, but without being not limited thereto, may mean an indirectly related object for obtaining information used in diagnosing the target disease.

As a specific example, when the target disease is a "stroke", a first diagnosis object DO may be the "face". This technology is also disclosed in Korean Patent No. 10-2274330 filed by Gachon University Industry-Academic Cooperation Foundation As another example, when the target disease is "thyroid eye disease", a first diagnosis object DO may be the "eyes", a second diagnosis object DO may be the "eyelids", and a third diagnosis object DO may be the "area including the eyes and the surrounding parts of the eyes". This technology is also disclosed in Korean Patent Application No. 10-2021-0085542 filed by the company (Thyroscope INC.).

The above-described examples of the diagnosis object DO are described to help a clear understanding of the concept of the diagnosis object DO described in the present specification. The diagnosis object DO is not limited to the above-described examples, and an object (target object, for example, a body part) related to a target disease to be diagnosed may be interpreted as a diagnosis object DO.

Hereinafter, in describing several embodiments of the present application, a description is based on the case in which the photographing device 1000 takes an image and the server 2000 verifies the captured image. However, this is specifically described with reference to an embodiment for convenience of description. The technical idea described in the present application is applicable to the case of solo operation by the server 2000 or the photographing device 1000, and also to the case of distributed operation by the photographing device 1000, the server 2000, and external devices. Therefore, the implementation form of the concept of the present disclosure is not limited to the embodiments described below.

Figure 3:
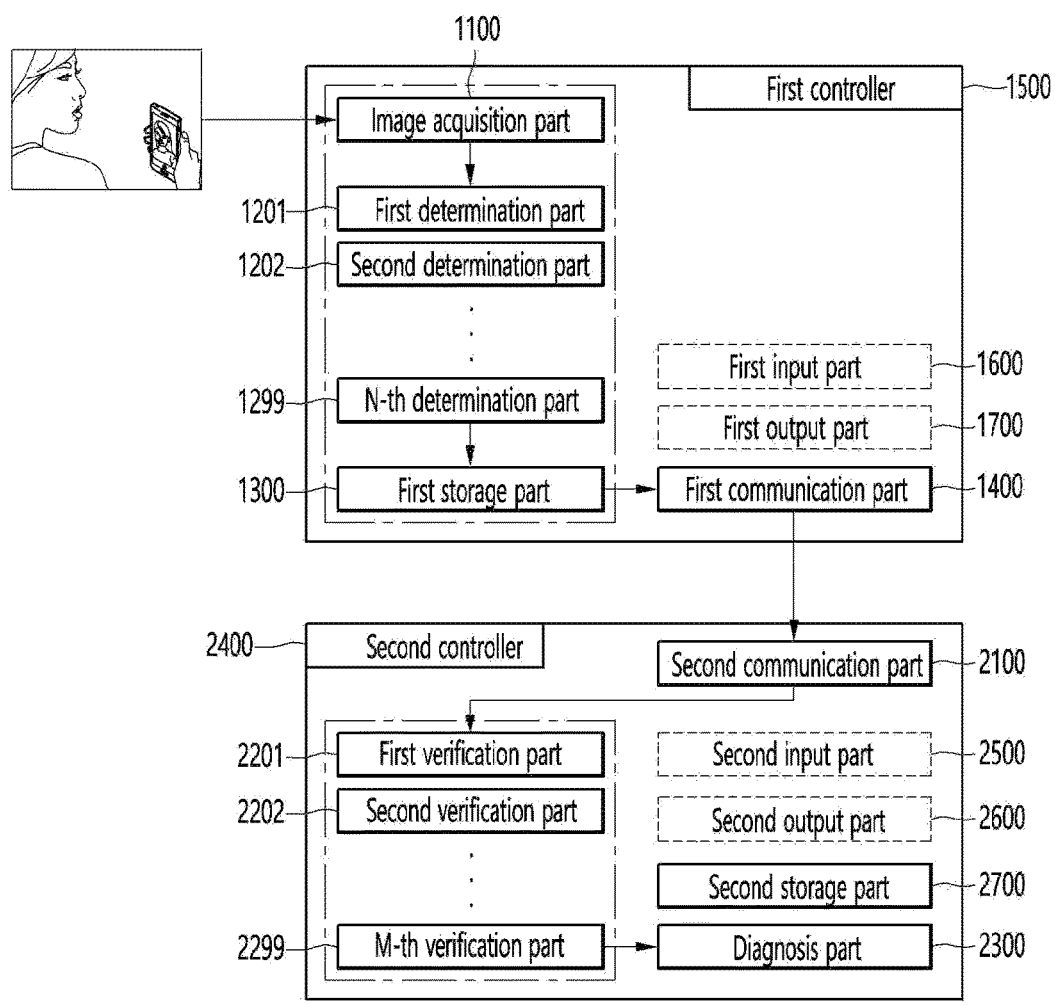
FIG. 3 is a diagram illustrating a configuration of a photographing device 1000 and a server 2000 according to an embodiment of the present application.

FIG. 3 is a diagram illustrating a configuration of the photographing device 1000 and the server 2000 according to an embodiment of the present application.

The photographing device 1000 may include an image acquisition part 1100, determination parts 1201, 1202, . . . , 1299, a first storage part 1300, a first communication part 1400, a first controller 1500, a first input part 1600, and a first output part 1700.

The image acquisition part 1100 may perform a function of taking images. According to an embodiment of the present application, the image acquisition part 1100 may obtain an image (for example, a preview image) according to a preset image frame. The image acquisition part 1100 may be a module, for example, a camera, suitable for taking images, or a function module for performing a function similar thereto.

The determination parts 1201, 1202, . . . , 1299 may perform a function of determining whether the target image satisfies the photographing conditions. According to an embodiment of the present application, the determination parts 1201, 1202, . . . , 1299 may determine whether the image obtained through the image acquisition part 1100 satisfies the photographing conditions.

The photographing device 1000 may include the one or more determination parts 1201, 1202, . . . , 1299. According to an embodiment of the present application, a first determination part 1201 may determine whether a first photographing parameter of the target image satisfies a first photographing condition, a second determination part 1202 may determine whether a second photographing parameter of the target image satisfies a second photographing condition, and an N-th determination part may determine whether an N-th photographing parameter of the target image satisfies an N-th photographing condition. Herein, N may be a natural number equal to or greater than 2. This means that there are several items evaluated with the photographing parameters, and means that there may be one or two items evaluated with the photographing parameters.

According to an embodiment of the present application, the first photographing parameter and the second photographing parameter may be different from each other. For example, the first photographing parameter may be related to a diagnosis object DO, and the second photographing parameter may be related to the brightness of a picture.

According to an embodiment of the present application, the first photographing parameter and the second photographing parameter may be the same, and the first photographing condition corresponding to the first photographing parameter and the second photographing condition corresponding to the second photographing parameter may be difference from each other. For example, both the first photographing parameter and the second photographing parameter may be related to a diagnosis object DO, the first photographing condition may be a criterion related to the position of the diagnosis object DO, and the second photographing condition may be a criterion related to whether the diagnosis object DO is detected.

The one or more determination parts 1201, 1202, . . . , 1299 included in the photographing device 1000 determines whether the target image satisfies the respective photographing conditions. When the determination parts 1201, 1202, . . . , 1299 determine that the target image satisfies all the pre-stored photographing conditions, the first controller 1500 may store the captured image by using the image acquisition part 1100.

The first storage part 1300 may store therein various types of data and programs required for the photographing device 1000 to operate. In order to keep data regardless of whether or not system power is provided, the first storage part 1300 may be realized as a non-volatile memory, such as flash memory, or a hard-disc drive. According to an embodiment of the present application, the first storage part 1300 may store therein an algorithm for obtaining the photographing parameters, the photographing conditions corresponding to the photographing parameters, a program for determining whether the photographing parameters satisfy the stored photographing conditions, and/or captured images.

According to an embodiment of the present application, an image analysis algorithm for detecting a diagnosis object DO may be stored in the first storage part 1300. In other words, the first storage part 1300 stores therein the image analysis algorithm for detecting the photographing parameters related to the diagnosis object DO, and the conditions corresponding thereto. For example, a first image analysis algorithm may be a landmark image analysis algorithm. As another example, the first image analysis algorithm may be a pose estimation algorithm. As still another example, the first image analysis algorithm may be a color comparison algorithm.

The first communication part 1400 may perform transmission and reception of data so that the photographing device 1000 performs bi-directional communication with external devices, such as the server, etc. The first communication part 1400 may access the external devices (for example, the server 2000) through a wired/wireless wide/local area network or local access method according to a preset communication protocol.

The first communication part 1400 may be realized by a group of access ports or access modules for respective devices, so protocols for access or the external devices to be accessed are not limited to one type or format. The first communication part 1400 may be built in the photographing device 1000, or the entire or some of the construction may be additionally provided in the form of an add-on or a dongle to the photographing device 1000.

The first controller 1500 may perform a function of managing and controlling the overall operation of the photographing device 1000. The first controller 1500 may perform operation and processing of various types of information, and may control the operation of elements of a terminal.

The first controller 1500 may be realized as a computer or a similar device according to hardware, software, or a combination thereof. In terms of hardware, the first controller 1500 may be provided in the form of an electronic circuit, such as a CPU chip, for performing a control function by processing electrical signals. In terms of software, the first controller 1500 may be provided in the form of a program for driving the hardware first controller 1500.

According to an embodiment of the present application, the first controller 1500 may determine, through the determination parts 1201, 1202, . . . , 1299, whether the image obtained by the image acquisition part 1100 satisfies the conditions stored in the first storage part 1300. In addition, when it is determined that the image satisfies the pre-stored photographing condition(s), the first controller 1500 may store the captured image in the first storage part 1300, and may transmit the same to the server 2000 through the first communication part 1400.

The photographing device 1000 according to an embodiment of the present application may include the first input part 1600 and/or the first output part 1700.

The first input part 1600 may perform a function of obtaining information from a user. The first input part 1600 may receive a user input from the user. The user input may be a key input, a touch input, and/or a voice input, but without being limited thereto, may be provided in various forms.

The first input part 1600 may be realized as a user input device that is generally used. As an example, the first input part 1600 may be a touch sensor for detecting a user's touch, but is not limited thereto. Herein, the "touch sensor" may mean a piezoelectric or capacitive touch sensor for detecting a touch through a touch panel or a touch film attached on a display panel, and/or an optical touch sensor for detecting a touch by an optical method.

The first output part 1700 may perform a function of outputting information so that a user can check the information. The first output part 1700 may output the information obtained from a user, obtained and/or processed from the external devices. The output of the information may be visual, audible, and/or tactual output, but without being limited thereto, may be provided in various forms.

The first output part 1700 may be realized as a user output device that is generally used. For example, the first output part 1700 may be a display for outputting images, and/or a speaker for outputting sounds, but is not limited thereto. Herein, the "display" may refer to an image display device in a broad sense, including a liquid-crystal display (LCD), a light-emitting diode (LED) display, an organic light-emitting diode (OLED) display, a flat panel display (FPD), a transparent display, a curved display, a flexible display, a 3D display, a holographic display, a projector, and/or other various types capable of performing an image output function.

The first output part 1700 may be integrated with the first input part 1600. For example, when the first output part 1700 is a display, the first output part 1700 may be in the form of a touch display integrated with a touch sensor that is the first input part 1600.

The server 2000 may include a second communication part 2100, verification parts 2201, 2202, . . . , 2299, a diagnosis part 2300, a second controller 2400, a second input part 2500, a second output part 2600, and a second storage part 2700.

Similarly to the above-described first communication part 1400, the second communication part 2100 may perform a function of exchanging data with the external devices. For example, the second communication part 2100 may receive the captured image through the first communication part 1400. Specifically, the second communication part 2100 may receive the captured image and position information of the diagnosis object DO in the captured image through the first communication part 1400.

The verification parts 2201, 2202, . . . , 2299 may perform a function of determining whether the target image satisfies the verification conditions. According to an embodiment of the present application, the verification parts 2201, 2202, . . . , 2299 may determine whether the captured image received through the second communication part 2100 satisfies the verification conditions.

The server 2000 may include the one or more verification parts 2201, 2202, . . . , 2299. According to an embodiment of the present application, a first verification part 2201 may determine whether a first verification parameter of the captured image satisfies a first verification condition, a second verification part 2202 may determine whether a second verification parameter satisfies a second verification condition, and an M-th verification part 2299 may determine whether an M-th verification parameter satisfies an M-th verification condition. Herein, M may be a natural number equal to or greater than 2. This means that there are several items evaluated with the verification parameters, and means that there may be one or two items evaluated with the verification parameters.

The first verification parameter and the second verification parameter may be different from each other. For example, the first verification parameter may be related to a diagnosis object DO, and the second verification parameter may be related to the brightness of a picture.

The first verification parameter and the second verification parameter may be the same, and the first verification condition corresponding to the first verification parameter and the second verification condition corresponding to the second verification parameter may be different from each other. For example, both the first verification parameter and the second verification parameter may be related to a diagnosis object DO, the first verification condition may be a criterion related to the position of the diagnosis object DO, and the second verification condition may be a criterion related to whether the diagnosis object DO is detected.

The server 2000 may evaluate the verification parameters and the verification conditions that correspond to the photographing parameters and the photographing conditions evaluated by the photographing devices 1000. As a specific example, the first photographing parameter and the first verification parameter may be the same, and the first photographing condition corresponding to the first photographing parameter and the first verification condition corresponding to the first verification parameter may be the same.

According to an embodiment of the present application, the photographing conditions already determined by the photographing device 1000 are evaluated once more as the verification conditions by the server 2000, thereby preventing the accuracy of diagnosis by the diagnostic device itself from being degraded because of the lack of quality (or accuracy) of a diagnostic image.

The server 2000 may not evaluate some of the photographing parameters and the photographing conditions evaluated by the photographing device 1000, as the verification parameters and the verification conditions. As a specific example, the second photographing parameter and the second verification parameter may be different from each other.

According to an embodiment of the present application, it is not necessary to perform verification through the verification conditions on the parameters already determined with the photographing conditions unless the parameters are related to a diagnosis object DO, so the second photographing parameter and the second verification parameter may not be the same. In this case, when the photographing device 1000 may evaluate the first to the N-th photographing parameter and the server 2000 may evaluate the first to the M-th verification parameter, N may be a larger number than M.

The one or more verification parts 2201, 2202, . . . , 2299 included in the server 2000 may determine whether the target image satisfies the respective verification conditions. When the verification parts 2201, 2202, . . . , 2299 determine that the captured image satisfies all the pre-stored verification conditions, the second controller 2400 may determine the captured image as a diagnostic image and perform the operation for obtaining diagnosis assistance information through the diagnosis part 2300, or may store the diagnostic image through the second storage part 2700.

The diagnosis part 2300 may perform a function of obtaining the diagnosis assistance information by using an image. The diagnosis part 2300 may perform a function of obtaining information (for example, the diagnosis assistance information) on a target disease on the basis of the diagnostic image by using a diagnostic algorithm stored in the second storage part 2700. As a specific example, the second storage part 2700 may store therein the diagnostic model that is trained using both an image including the diagnosis object DO and information on whether the target disease has occurred, and the diagnosis part 2300 may perform the function of obtaining the diagnosis assistance information on the basis of the diagnostic model and the diagnostic image under control by the second controller 2400. The diagnostic model may mean an artificial intelligence model in which functions and/or parameters are stored.

According to another embodiment of the present application, the diagnosis part 2300 may be included in a separate server, and the server 2000 may obtain the diagnosis assistance information by transmitting the diagnostic image to the separate server through the second communication part 2100.

Similarly to the first controller 1500, the second controller 2400 may perform a function of managing and controlling the operation of the server 2000. Similarly to the first input part 1600, the second input part 2500 may perform a function of obtaining information from a user. Similarly to the first output part 1700, the second output part 2600 may perform a function of outputting information so that a user can check the information.

Similarly to the first storage part 1300, the second storage part 2700 may store therein various types of data and programs required for the server 2000 to operate.

According to an embodiment of the present application, the second storage part 2700 may be in the form of a database. The database is structured for each keyword category, and desired information may be found with a specific keyword. The structured database may be realized in various ways according to the design and construction method of the database, so a detailed description of the structured database will be omitted.

According to an embodiment of the present application, an image analysis algorithm for detecting a diagnosis object DO may be stored in the second storage part 2700. In other words, the second storage part 2700 stores therein the image analysis algorithm for detecting the verification parameters related to the diagnosis object DO, and the conditions corresponding thereto. For example, a second image analysis algorithm may be a landmark image analysis algorithm. As another example, the second image analysis algorithm may be a pose estimation algorithm. As still another example, the second image analysis algorithm may be a color comparison algorithm.

According to an embodiment, the image analysis algorithm stored in the server 2000 and the image analysis algorithm stored in the user terminal 1000 may be algorithms for detecting the same object. However, the amount of operation of the image analysis algorithm stored in the server 2000 and the amount of operation of the image analysis algorithm stored in the user terminal 1000 may be different from each other. As a specific example, the two image analysis algorithms may be selected such that the amount of operation of the image analysis algorithm in the user terminal 1000 that needs to perform real-time operation while taking a picture is less than the amount of operation of the image analysis algorithm in the server 2000.

A description of redundant functions/modules related to the second controller 2400, the second input part 2500, the second output part 2600, and the second storage part 2700 will be omitted.

The server 2000 according to an embodiment of the present application may be a single server that is physically one, or a distributed server in which the throughput or role is distributed over a plurality of servers.

Hereinafter, unless otherwise specified, the operation of the photographing device 1000 may be interpreted as being performed by the first controller 1500, and the operation of the server 2000 may be interpreted as being performed by the second controller 2400.

Hereinafter, the operation of the photographing device 1000 (hereinafter, referred to as a user terminal) and/or the server 2000 according to several embodiments of the present application will be described in detail.

Figure 4:
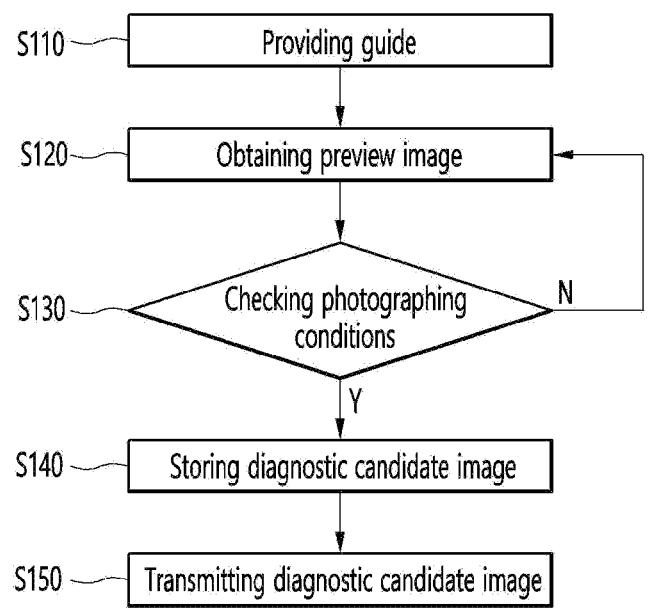
FIG. 4 is a flowchart illustrating a captured image acquisition operation of a user terminal 1000 according to an embodiment of the present application.

FIG. 4 is a flowchart illustrating a captured image acquisition operation of the user terminal 1000 according to an embodiment of the present application.

The user terminal 1000 may provide a guide in step S110, may obtain a preview image in step S120, may perform determination with respect to the photographing conditions in step S130, may store a diagnostic candidate image in step S140, and may transmit the diagnostic candidate image in step S150.

The first controller 1500 of the user terminal 1000 may perform control in step S110 such that the guide is provided using the first output part 1700.

Herein, the guide performs a function of assisting in taking an image. For example, the guide may be in the form of a line or letter output together in the preview image being output on the display of the user terminal 1000. As another example, the guide may be in the form of voice output to assist in photographing through the speaker of the user terminal 1000. However, no limitation thereto is imposed.

The guide may be provided to assist some of the several photographing parameters set for the photographing conditions, or may be provided to assist all the photographing parameters set for the photographing conditions. The photographing parameters assisted by the guide may include a photographing parameter related to a diagnosis object DO.

The guide may be provided in the form of presenting the photographing conditions corresponding to the photographing parameters, or may be provided in the form of visualizing the current state of a photographed person, or may be provided in the form of outputting both the photographing conditions and the current state. As a specific example, the guide provided on the user terminal may include a first guide for showing the appropriate positions of the eyes, and a second guide for showing the current positions of the eyes.

Figure 5:
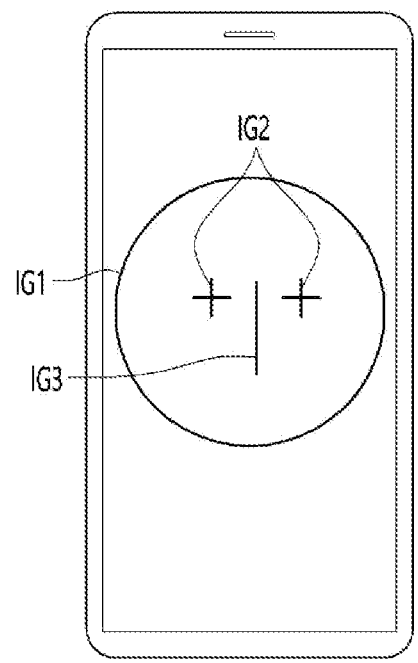
FIG. 5 is a diagram illustrating a first output part 1700 of the user terminal 1000 in a guide provision operation S110 according to an embodiment of the present application.

FIG. 5 is a diagram illustrating the first output part 1700 of the user terminal 1000 in the guide provision operation S110 according to an embodiment of the present application.

The guide output on the user terminal 1000 may include a first guide IG1, a second guide IG2, and a third guide IG3. The first guide IG1 may be an indicator for guidance to position a user's face inside the first guide IG1 so that the user's face is kept at an appropriate distance from the user terminal 1000. The second guide IG2 may be an indicator for inducing the alignment of the positions of the user's eyes and the second guide IG2 so as to obtain an image in which the user's eyes are at determined positions. The third guide IG3 may be an indicator for guidance on the position at which the user's nose line needs to be so that the left-right angle (yaw) of the user's face is not out of a pre-stored criterion.

According to an embodiment of the present application, when the guide shown in FIG. 5 is provided in taking an image for diagnosing (predicting) thyroid eye disease, the second guide IG2 may be a guide related to a diagnosis object DO.

Referring back to FIG. 4, the first controller 1500 of the user terminal 1000 may perform control in step S120 such that the preview image is obtained using the image acquisition part 1100.

Herein, the preview image may mean an image obtained according to a determined frame rate in the image photographing step. Specifically, an image photographing operation starts according to a user input or an automatic photographing operation starts as the pre-stored conditions are satisfied, and in response thereto, a captured image is stored, wherein an image captured before this storing step may mean the preview image.

The first controller 1500 of the user terminal 1000 may use the determination parts 1201, 1202, . . . , 1299 to determine whether the obtained preview image satisfies the photographing conditions.

When it is determined that the target image (for example, the preview image to be checked) satisfies the photographing conditions, the first controller 1500 of the user terminal 1000 may use the first storage part 1300 to store the captured image in step S140, and may use the first communication part 1400 to transmit the captured image to the server 2000 in step S150.

When it is determined that the target image does not satisfy the photographing conditions, the first controller 1500 of the user terminal 1000 may use the determination parts 1201, 1202, . . . , 1299 to determine whether another image obtained in step S120 satisfies the photographing conditions in step S130.

Figure 6:
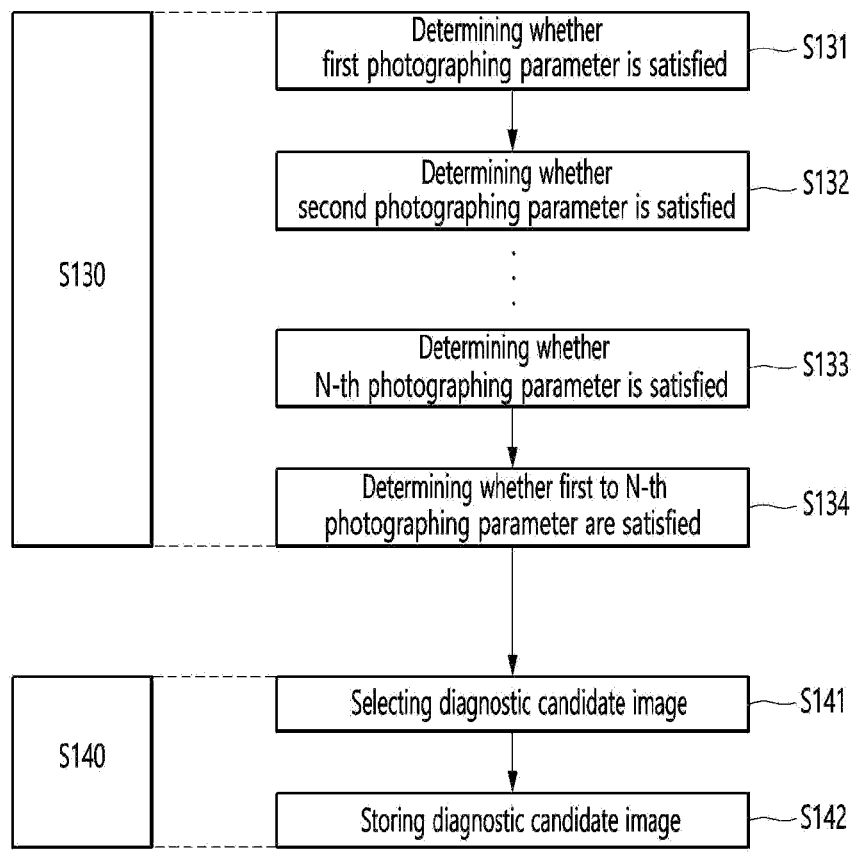
FIG. 6 is a diagram specifically illustrating a method S130 of determining whether photographing conditions are satisfied according to an embodiment of the present application.

FIG. 6 is a diagram specifically illustrating a method S130 of determining whether the photographing conditions are satisfied according to an embodiment of the present application.

The first storage part 1300 may store therein the one or more photographing parameters to be determined to evaluate whether the target image satisfies the photographing conditions, and the conditions corresponding to the photographing parameters. The photographing parameter evaluated when it is determined whether the photographing conditions are satisfied in step S130 may be one photographing parameter related to the diagnosis object DO, or a plurality of the photographing parameters in which at least some of the parameters are related to the diagnosis object DO.

According to an embodiment of the present application, the photographing conditions related to the diagnosis object DO may be related to the whole detection of the diagnosis object DO. For example, when the diagnosis object DO is the "eyes", the first controller 1500 may evaluate whether the eyes are wholly (that is, entirely) detected in the preview image. As another example, when the diagnosis object DO is the "entire body", the first controller 1500 may evaluate whether all the determined joints are detected in the preview image.

According to an embodiment of the present application, the photographing conditions related to the diagnosis object DO may be determined by comparing the diagnosis object DO with a pre-stored reference area. For example, the photographing conditions related to the diagnosis object DO may be set to be satisfied when a detection area of the diagnosis object DO is positioned at a target area. As a specific example, when the diagnosis object DO is the "eyes", the first controller 1500 may evaluate whether the outlines of the detected eyes are overlaid with areas stored as the positions of the eyes.

Figure 7:
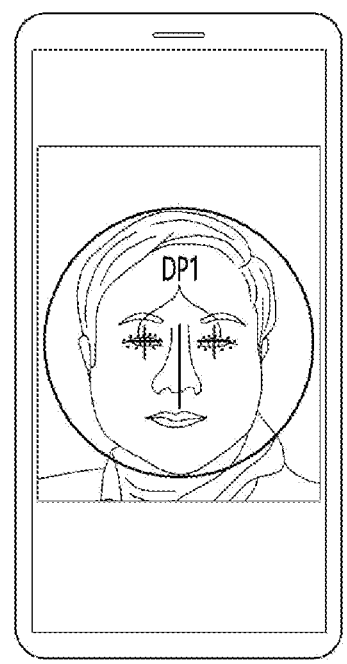
FIG. 7 is a diagram illustrating photographing parameters according to an embodiment of the present application.

FIG. 7 is a diagram illustrating the photographing parameters according to an embodiment of the present application.

As a specific example, when the first photographing parameter DP1 is landmarks of the eyes in the image obtained by driving the landmark detection algorithm, the landmarks of both eyes in the preview image may be obtained as the first photographing parameter DP1 as shown in FIG. 7. The first controller 1500 may compare the first photographing parameter DP1 with the second image guide IG2. Alternatively, the first controller 1500 may compare the first photographing parameter DP1 with the pre-stored eye positions. The first controller 1500 evaluates whether the outlines (that is, the first photographing parameter DP1) of the detected eyes are overlaid with the areas stored as the positions of the eyes, and may determine whether the first photographing parameter DP1 satisfies the first photographing condition.

As another specific example, when the diagnosis object DO is the "eyes", the first controller 1500 may evaluate whether the centers of the outlines of the detected eyes are included in areas stored as the positions of the pupils.

According to an embodiment of the present application, the photographing parameters evaluated when it is determined whether the photographing conditions are satisfied in step S130 may include a general indicator related to photographing quality. For example, the first controller 1500 may evaluate whether the ambient brightness at the point in time when the target image is obtained is equal to or greater than a reference value. As another example, the first controller 1500 may evaluate whether an acceleration sensor value of the user terminal at the point in time when the target image is obtained is equal to or greater than a reference value.

Referring back to FIG. 6, when it is determined whether the target image satisfies the photographing conditions in step S130, whether each of the preset photographing parameters is satisfied may be evaluated.

As a specific example, the first controller 1500 may use the first determination part 1201 to analyze the preview image, may obtain the first photographing parameter, and may evaluate whether the first photographing condition corresponding to the first photographing parameter is satisfied in step S131.

The first controller 1500 may use the second determination part 1202 to analyze the preview image, may obtain the second photographing parameter, and may evaluate whether the second photographing condition corresponding to the second photographing parameter is satisfied in step S132.

The first controller 1500 may use the N-th determination part 1299 to analyze the preview image, may obtain the N-th photographing parameter, and may evaluate whether the N-th photographing condition corresponding to the N-th photographing parameter is satisfied in step S133.

The determining of whether the first photographing condition corresponding to the first photographing parameter is satisfied in step S131, the determining of whether the second photographing condition corresponding to the second photographing parameter is satisfied in step S132, . . . , and the determining of whether the N-th photographing condition corresponding to the N-th photographing parameter is satisfied in step S133 may be performed sequentially or in parallel.

According to an embodiment of the present application, when it is determined that all of the first photographing parameter to the N-th photographing parameter satisfy the first condition to the N-th condition respectively, the first controller 1500 may store the captured image. In this case, a condition in which all of the first condition to the N-th condition are satisfied may be defined as a pre-stored condition. That is, the first controller 1500 may store the captured image, when it is determined that the pre-stored condition is satisfied. To be more specific, satisfying the pre-stored condition may mean that all of the first photographing parameter to the N-th photographing parameter satisfy the first condition to the N-th condition respectively.

According to another embodiment of the present application, when it is determined that some of the first photographing parameter to the N-th photographing parameter satisfy the first condition to the N-th condition respectively, the first controller 1500 may store the captured image. In this case, a condition in which some of the first condition to the N-th condition are satisfied may be defined as a pre-stored condition. That is, the first controller 1500 may store the captured image, when it is determined that the pre-stored condition is satisfied. To be more specific, satisfying the pre-stored condition may mean that some of the first photographing parameter to the N-th photographing parameter satisfy the first condition to the N-condition respectively.

The pre-stored condition is not limited to the above-described embodiments. For example, when only the first photographing parameter is obtained, a condition in which the first condition is satisfied may be defined as a pre-stored condition.

According to an embodiment of the present application, the first storage part 1300 may store therein the algorithm for detecting the several photographing parameters evaluated when determining whether the photographing conditions are satisfied in step S130, and the amounts of operation and/or processing speeds of the algorithm for detecting the respective photographing parameters may be different from each other.

Figure 8:
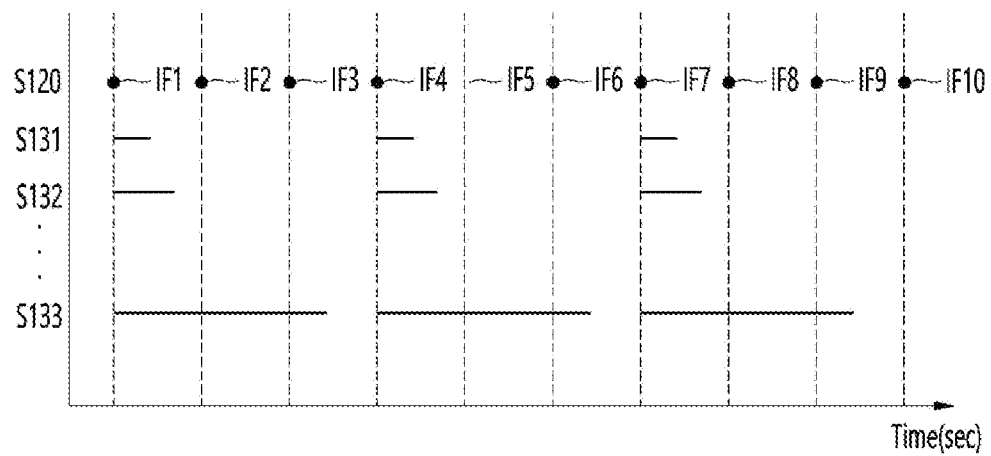
Figure 9:
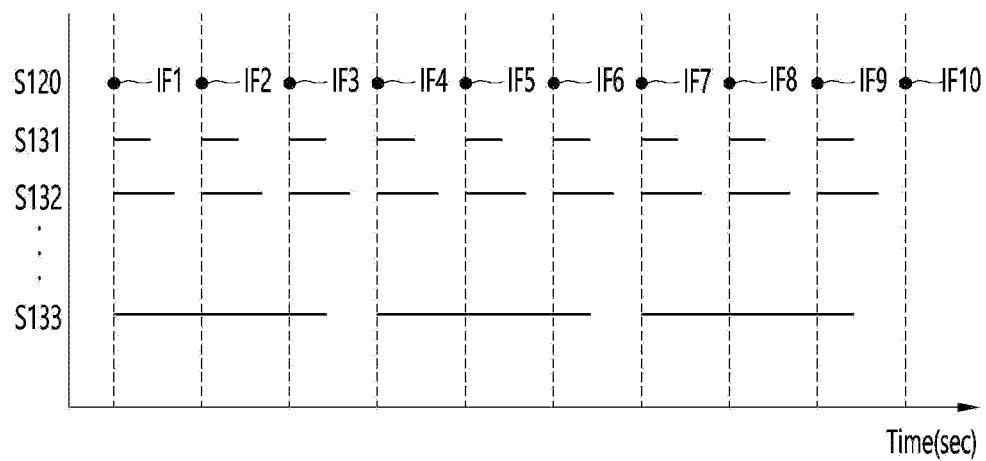

FIGS. 8, 9 and 10 are diagrams specifically illustrating an evaluation target image, the frequency of evaluations of the photographing parameters, and a stored captured image according to the speed of determining whether the condition corresponding to each photographing parameter is satisfied.

The user terminal 1000 may obtain a preview image according to the preset frame rate. Preferably, when whether the condition corresponding to each photographing parameter is satisfied is determined within the break time between the time when a preview image is obtained and the time when the next preview image is obtained, whether the conditions corresponding to the photographing parameters are satisfied may be evaluated for each preview image.

However, when the user terminal 1000 is unable to determine whether the condition corresponding to at least one of the several photographing parameter is satisfied within the break time between the time when a preview image is obtained and the time when the next preview image is obtained, it is necessary to set determination periods for the photographing conditions for the respective photographing parameters, and a reference of the relationship between the determination periods.

According to an embodiment of the present application, the determination periods of the photographing parameters may be synchronized on the basis of the photographing parameter that requires the longest time that it takes to determine whether the condition for the photographing parameter is satisfied.

Referring to FIG. 8, a first image frame IF1, a second image frame IF2, a third image frame IF3, . . . , a 10th image frame IF10 may be obtained according to the preset frame rate.

Assuming that the operation S133 of evaluating whether the N-th photographing parameter for the first image frame IF1 is satisfied is completed after the first image frame IF1 is obtained, the second image frame IF2 is obtained, and before the third image frame IF3 is obtained, all the first photographing parameter to the N-th photographing parameter may be designed to evaluate whether the condition for each photographing parameter is satisfied, once per three image frames.

It may be evaluated whether the first image frame IF1, the fourth image frame IF4, the seventh image frame IF7, and the 10th image frame IF10 satisfy the conditions for the respective photographing parameters, and it may not be evaluated whether the second image frame IF2, the third image frame IF3, the fifth image frame IF5, the sixth image frame IF6, etc. satisfy the conditions for the respective photographing parameters.

According to another embodiment of the present application, regarding the photographing parameters, each photographing parameter may independently have the time that it takes to determine whether the condition is satisfied, and whether the conditions for the respective photographing parameters are satisfied may be evaluated in parallel.

Referring to FIG. 9, a first image frame IF1, a second image frame IF2, a third image frame IF3, . . . , a 10th image frame IF10 may be obtained according to the preset frame rate.

The operation S131 of evaluating whether the first photographing parameter is satisfied may be performed every frame. The operation S132 of evaluating whether the second photographing parameter is satisfied may be performed every frame. The operation S133 of evaluating whether the N-th photographing parameter is satisfied may be performed every three image frames, and whether the condition is satisfied may be evaluated.

When it is evaluated whether the condition corresponding to each individual photographing parameter is satisfied according to the periods described with reference to FIG. 9, a result of determining whether the conditions are satisfied may be obtained as in the table shown in FIG. 10.

In determining S134 whether the first to the N-th photographing parameter are satisfied, determination may be based on whether the conditions corresponding to the first photographing parameter to the N-th photographing parameter are satisfied.

According to an embodiment of the present application, as shown in FIG. 10, the first controller 1500 may determine whether to store the captured image, on the basis of whether the latest first to N-th photographing parameters are satisfied. As a specific example, whether to store the captured image may be determined on the basis of whether the operation S131 for the ninth image frame IF9 is satisfied, whether the operation S132 for the ninth image frame IF9 is satisfied, and whether the operation S133 for the seventh image frame IF7 is satisfied.

According to another embodiment of the present application, the first controller 1500 may determine whether to store the captured image, on the basis of whether the first photographing parameter or the N-th photographing parameter are satisfied at least once within the latest determined periods. As a specific example, whether to store the captured image may be determined on the basis of whether the operation S131 for the seventh image frame IF7, the eighth image frame IF8, or the ninth image frame IF9 is satisfied, whether the operation S132 for the seventh image frame IF7, the eighth image frame IF8, or the ninth image frame IF9 is satisfied, and whether the operation S133 for the seventh image frame IF7 is satisfied.

Referring back to FIG. 6, when it is determined that the first to the N-th photographing parameter satisfy the respective conditions corresponding thereto, the diagnostic candidate image may be selected in step S141 and stored in step S142. The selecting of the diagnostic candidate image may correspond to the determining of the captured image.

According to an embodiment of the present application, the captured image (that is, the diagnostic candidate image) may be an image determined as satisfying the photographing conditions. Referring to FIG. 10, the seventh image frame IF7 may be stored as the captured image (that is, the diagnostic candidate image). According to another embodiment of the present application, the captured image (that is, the diagnostic candidate image) may be an image that is obtained immediately after it is determined that the photographing conditions are satisfied. Referring to FIG. 10, the 10th image frame IF10 may be stored as the captured image (that is, the diagnostic candidate image).

Referring back to FIG. 6, when it is determined that the first to the N-th photographing parameter do not satisfy the conditions, the photographing conditions for an image different from the image for which the photographing conditions have been checked may be checked. Herein, the image for which the photographing conditions are to be checked may be an image that is newly obtained after the image for which the photographing conditions are checked is obtained.

According to an embodiment of the present application, the image for which it is to be determined whether the photographing parameters are satisfied may be the next image of the image for which the photographing conditions have been checked. Referring to FIG. 10, after the photographing conditions for the first image frame IF1 are checked, the photographing conditions for the third image frame IF3 may be checked. According to another embodiment of the present application, the image for which it is to be determined whether the photographing parameters are satisfied may be an image that is first obtained after the time when it is determined whether the photographing conditions are satisfied on the basis of the first to the N-th photographing parameter. Referring to FIG. 10, after the photographing conditions for the first image frame IF1 are checked, the photographing conditions for the fourth image frame IF4 may be checked.

When the user terminal 1000 obtains the captured image, the user terminal 1000 may transmit the obtained captured image to the server 2000. The user terminal 1000 may transmit the captured image and information on at least some of the first photographing parameter to the N-th photographing parameter. For example, the user terminal 1000 may transmit the captured image and information on the detected position of the diagnosis object DO to the server 2000. As a specific example, when the diagnostic candidate image is a "facial image including the eyes" and information on the "positions of the eyes" is obtained through the image analysis algorithm, the information on the positions of the eyes and the facial image including the eyes may be transmitted to the server.

Figure 11:
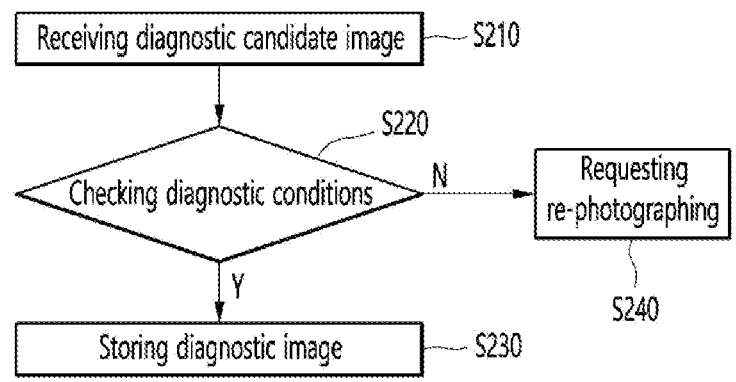
FIG. 11 is a flowchart illustrating an image verification operation of the server 2000 according to an embodiment of the present application.

FIG. 11 is a flowchart illustrating an image verification operation of the server 2000 according to an embodiment of the present application.

The second controller 2400 of the server 2000 may receive the diagnostic candidate image by using the second communication part 2100. The second controller 2400 of the server 2000 may receive the captured image by using the second communication part 2100.

According to an embodiment of the present application, the second controller 2400 may store, in the second storage part 2700, the captured image (that is, the diagnostic candidate image) and a detection value of the user terminal 1000 about the captured image. The detection value of the user terminal 1000 may be about the photographing parameters.

The second controller 2400 of the server 2000 may use the verification parts 2201, 2202, . . . , 2299 to determine whether the captured image (that is, the diagnostic candidate image) satisfies diagnostic conditions in step S220.

According to an embodiment of the present application, criteria for determining whether the diagnostic conditions are satisfied may correspond to all or some of the criteria determined as the photographing conditions. Determining whether the diagnostic conditions are satisfied includes a condition related to the diagnosis object DO in order to determine whether the captured image is allowed to be used as the diagnostic image. However, it is not necessary to determine all the photographing parameters determined with the photographing conditions again with the diagnostic conditions, so the criteria for determining whether the diagnostic conditions are satisfied may correspond to all or some of the criteria determined as the photographing conditions.

As a specific example, the diagnosis object DO with respect to the criteria for determining whether the diagnostic conditions are satisfied may be the same as the diagnosis object DO with respect to the criteria for determining whether the photographing conditions are satisfied. When the diagnosis object DO determined with the photographing conditions is the "entire body", the diagnosis object DO determined with the diagnostic conditions may also be the "entire body". When the diagnosis object DO determined with the photographing conditions is the "eyes", the diagnosis object DO determined with the diagnostic conditions may also be the "eyes".

When it is determined that the captured image (that is, the diagnostic candidate image) satisfies the diagnostic conditions, the second controller 2400 of the server 2000 may use the second storage part 2700 to store the image as the diagnostic image in step S230, and may use the diagnosis part 2300 to obtain the diagnosis assistance information. When it is determined that the captured image (that is, the diagnostic candidate image) does not satisfy the diagnostic conditions, the second controller 2400 of the server 2000 may request the user terminal S240 to perform re-photographing in step S240.

Figure 12:
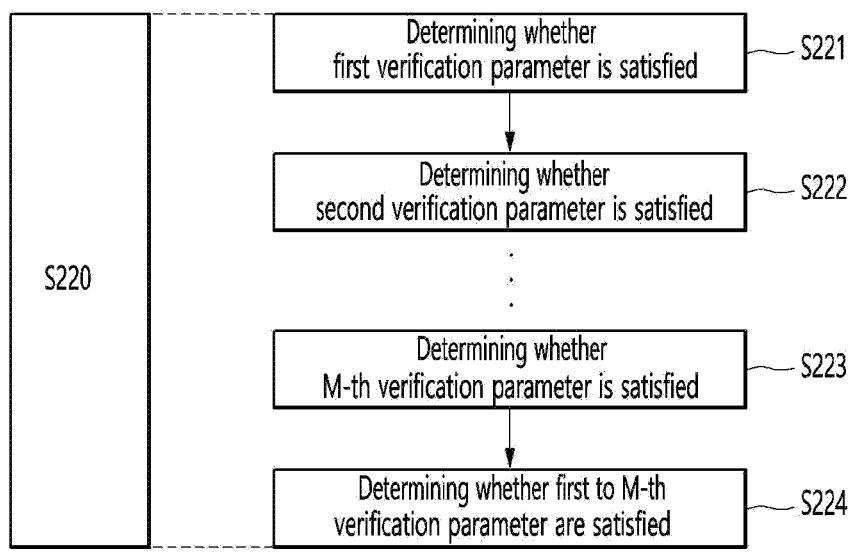
FIG. 12 is a diagram specifically illustrating a method S220 of determining whether verification conditions are satisfied according to an embodiment of the present application.

FIG. 12 is a diagram specifically illustrating a method S220 of determining whether the diagnostic conditions are satisfied according to an embodiment of the present application.

The second storage part 2700 may store therein the one or more verification parameters to be determined to evaluate whether the captured image satisfies the diagnostic conditions, and the conditions corresponding to the verification parameters. The verification parameter evaluated when it is determined whether the diagnostic conditions are satisfied in step S220 may be one verification parameter related to the diagnosis object DO, or a plurality of the verification parameters in which at least some of the parameters are related to the diagnosis object DO.

According to an embodiment of the present application, the verification conditions related to the diagnosis object DO may be related to the whole detection of the diagnosis object DO. For example, when the diagnosis object DO is the "eyes", the second controller 2400 may evaluate whether the eyes are wholly (that is, entirely) detected in the captured image. As another example, when the diagnosis object DO is the "entire body", the second controller 2400 may evaluate whether all the determined joints are detected in the captured image.

According to an embodiment of the present application, the verification conditions related to the diagnosis object DO may be determined by comparing the diagnosis object DO with the photographing parameters received from the user terminal 1000. For example, the verification conditions related to the diagnosis object DO may be set to be satisfied when the detection area of the diagnosis object DO obtained in the photographing condition check step is different from the detection area of the diagnosis object DO obtained in the verification condition check step by a threshold value or less.

As a specific example, when the diagnosis object DO is the "eyes", the second controller 2400 may evaluate whether the outlines of the eyes detected by the user terminal 1000 are present at the positions that are different from those of the outlines of the eyes detected by the server 2000 by the threshold value or less.

Figure 13:
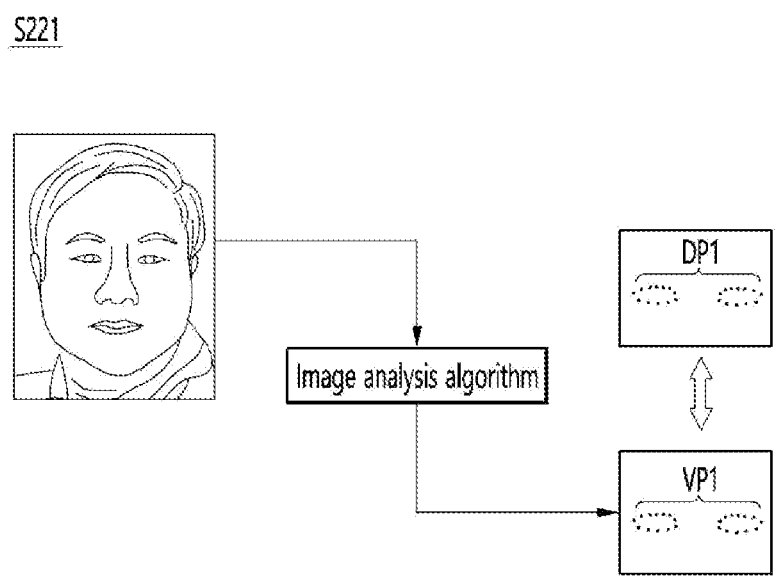
FIG. 13 is a diagram illustrating verification parameters according to an embodiment of the present application.

FIG. 13 is a diagram illustrating the verification parameters according to an embodiment of the present application.

When the first verification parameter VP1 is landmarks of the eyes in the image obtained by driving the landmark detection algorithm, the landmarks of both eyes in the captured image may be obtained as the first verification parameter VP1 as shown in FIG. 13.

The second controller 2400 may compare the first verification parameter VP1 with the first photographing parameter DP1. As a specific example, when the diagnosis object DO is the "eyes", the second controller 2400 may evaluate whether the outlines of the eyes detected as the first verification parameter VP1 are included in the outlines of the eyes detected as the first photographing parameter DP1 by the user terminal 1000.

Alternatively, the second controller 2400 may compare the first verification parameter VP1 with an area that is a criterion when the first photographing parameter DP1 is evaluated. As a specific example, when the diagnosis object DO is the "eyes", the second controller 2400 may evaluate whether the centers of the outlines of the eyes detected as the first verification parameter VP1 include the areas stored as the positions of the irises.

According to an embodiment of the present application, the verification parameters evaluated when it is determined whether the diagnostic conditions are satisfied in step S220 may include a general indicator related to photographing quality. For example, the second controller 2400 may evaluate whether the captured image includes an area corresponding to shaking because of the movement of the user terminal 1000 during photographing.

The amount of operation of the algorithm used in the server 2000 may be greater than that of the algorithm used in the user terminal 1000. This is because real-time photographing is performed when the user terminal 1000 checks the photographing parameters, so an algorithm requiring an excessive amount of operation is not suitable to be driven. As a result, in the process of obtaining the diagnostic image, the diagnosis object DO that has been analyzed with the photographing parameters is analyzed again by the server 2000, thereby obtaining an accurate picture.

According to an embodiment of the present application, the image analysis algorithm for detecting the diagnosis object DO in the server 2000 and the image analysis algorithm for detecting the diagnosis object DO in the user terminal 1000 may be different types of image analysis algorithms. As a specific example, the image analysis algorithm for detecting the diagnosis object DO in the server 2000 may be an image segmentation algorithm, and the image analysis algorithm for detecting the diagnosis object DO in the user terminal 1000 may be a landmark detection algorithm.

According to another embodiment of the present application, the image analysis algorithm for detecting the diagnosis object DO in the server 2000 and the image analysis algorithm for detecting the diagnosis object DO in the user terminal 1000 may be the same type of image analysis algorithms, and the amount of operation of the image analysis algorithm in the user terminal 1000 may be smaller than the amount of operation of the image analysis algorithm in the server 2000. As a specific example, the image analysis algorithm for detecting the diagnosis object DO in the server 2000 may use get_frontal_face_detector of Dlib™ for landmark detection, and the image analysis algorithm for detecting the diagnosis object DO in the user terminal 1000 may use ML kit—face detection of Google™ for landmark detection, but no limitation thereto is imposed.

Referring back to FIG. 12, when it is determined whether the captured image satisfies the diagnostic conditions in step S220, whether each of the predetermined verification parameters is satisfied may be evaluated.

As a specific example, the second controller 2400 may use the first verification part 2201 to analyze the captured image, may obtain the first verification parameter, and may evaluate whether the first verification condition corresponding to the first verification parameter is satisfied in step S221.

The second controller 2400 may use the second verification part 2202 to analyze the captured image, may obtain the second verification parameter, and may evaluate whether the second verification condition corresponding to the second verification parameter is satisfied in step S222.

The second controller 2400 may use the M-th verification part 2299 to analyze the captured image, may obtain the M-th verification parameter, and may evaluate whether the M-th verification condition corresponding to the M-th verification parameter is satisfied in step S223.

The determining of whether the first verification condition corresponding to the first verification parameter is satisfied in step S221, the determining of whether the second verification condition corresponding to the second verification parameter is satisfied in step S222, . . . , and the determining of whether the M-th verification condition corresponding to the M-th verification parameter in step S223 may be performed sequentially or in parallel.

When it is determined that all the first verification parameter to the M-th verification parameter are satisfied, the second controller 2400 may store the captured image as the diagnostic image in step S230. Storing the diagnostic image may mean that the captured image is determined as a target image from which the diagnosis assistance information is to be obtained, or may mean that the captured image is stored after preprocessing required to obtain the diagnosis assistance information is applied.

When the captured image is determined as the target image from which the diagnosis assistance information is to be obtained, the server 2000 may obtain the diagnosis assistance information on the target image through the diagnosis part 2300. However, without being limited thereto, it is also possible to realize a form in which the captured image may be transmitted to a doctor so that the doctor can perform telemedicine.

According to another embodiment of the present application, When the target image is used as the diagnostic image, the image may be cropped and stored with reference to the verification parameters associated with the diagnosis object DO. A detailed description thereof will be described below with reference to FIG. 14.

According to an embodiment of the present application, when it is determined that the first to the M-th verification parameter do not satisfy the conditions, the user terminal 1000 may be requested to perform re-photographing. According to another embodiment of the present application, when it is determined that the first to the M-th verification parameter do not satisfy the conditions, but the position of the diagnosis object DO detected by the user terminal 1000 and the position of the diagnosis object DO detected by the server 2000 are slightly different from each other, postprocessing of the captured image may be performed in the form of parallel movement such that the position of the diagnosis object DO detected by the server 2000 is placed in the reference area.

Figure 14:
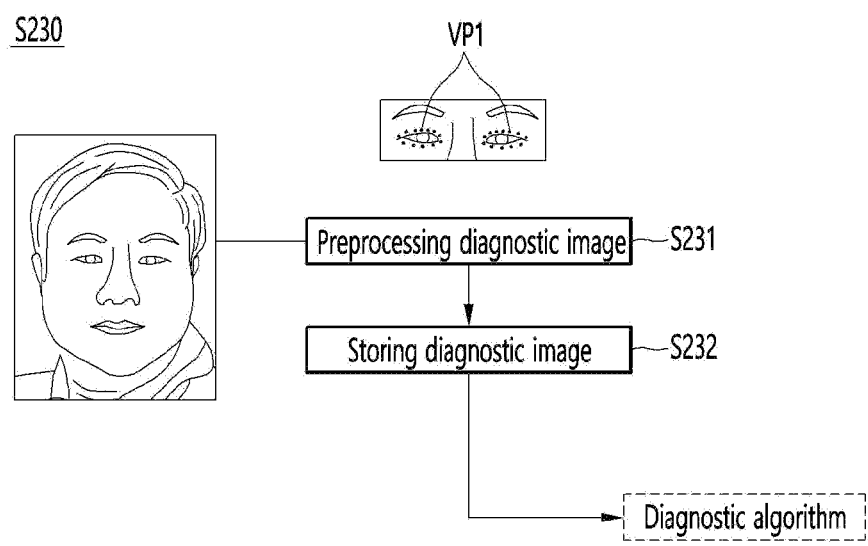
FIG. 14 is a diagram illustrating an operation of storing a diagnostic image and of acquiring diagnosis assistance information by using the same according to an embodiment of the present application.

FIG. 14 is a diagram illustrating an operation of storing the diagnostic image and of acquiring the diagnosis assistance information by using the same according to an embodiment of the present application.

The second controller 2400 may perform preprocessing on the captured image in step S231 to obtain the diagnostic image, and may store the obtained diagnostic image in step S232. In addition, the second controller 2400 may apply the diagnostic image to the diagnostic algorithm to obtain information on the target disease.

The preprocessing performed on the captured image may be in the form of performing cropping such that an area other than the area of the diagnosis object DO is not used as noise in the diagnostic algorithm.

The second controller 2400 may preprocess the diagnostic image on the basis of the verification parameters related to the diagnosis object DO in step S231. As a specific example, the second controller 2400 may obtain the diagnostic image by performing cropping with reference to the first verification parameter VP1 that is the verification parameter related to the diagnosis object DO such that only the area including the diagnosis object DO remains. Alternatively, the second controller 2400 may preprocess the diagnostic image on the basis of the verification parameters related to the diagnosis object DO and the photographing parameters related to the diagnosis object DO in step S231.

The specific method of obtaining a diagnostic image used for diagnosis has been described. The above-described method of obtaining a diagnostic image may be applied to any diagnostic devices of obtaining information on a disease by analyzing an image.

Hereinafter, the technical idea disclosed in the present application will be clarified with reference to several specific embodiments in order to help understanding of the above-described method of obtaining a diagnostic image.

The user terminal 1000 may evaluate whether at least the first photographing parameter satisfies the first photographing condition. The first photographing parameter may be related to a diagnosis object DO. The user terminal 1000 may obtain the first photographing parameter on the basis of a preview image, and may evaluate whether the obtained first photographing parameter satisfies the first photographing condition.

When the first photographing parameter is obtained, a first image analysis algorithm may be used. The first image analysis algorithm may be a detection model trained by labeling the diagnosis object DO in an image.

The user terminal 1000 may obtain the first photographing parameter on the basis of a preview image, and may evaluate whether the obtained first photographing parameter satisfies the first photographing condition, and may obtain a captured image when it is evaluated that the first photographing condition is satisfied.

The user terminal 1000 may transmit the captured image and an analysis value of the first image analysis algorithm to a server 2000.

The server 2000 may evaluate whether at least a first verification parameter satisfies a first verification condition. The first verification parameter may be related to the diagnosis object DO. The server 2000 may obtain the first verification parameter on the basis of the captured image, and may evaluate whether the obtained first verification parameter satisfies the first verification condition.

When the first verification parameter is obtained, a second image analysis algorithm may be used. The second image analysis algorithm may be a detection model trained by labeling the diagnosis object DO in an image.

The server 2000 may obtain the first verification parameter on the basis of the captured image, and may evaluate whether the obtained first verification parameter satisfies the first verification condition, and may store the captured image as the diagnostic image when it is evaluated that the first verification condition is satisfied.

Figure 15A:
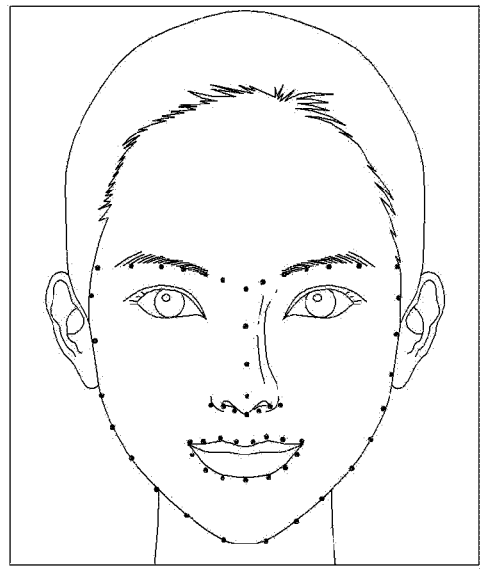
FIGS. 15A and 15B are diagrams illustrating a method of an eye disease-related image according to an embodiment of the present application.
Figure 15B:
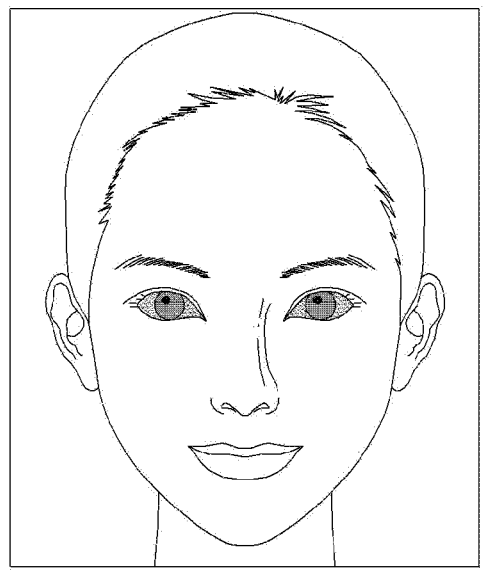

FIGS. 15A and 15B are diagrams illustrating a method of an eye disease-related image according to an embodiment of the present application.

According to an embodiment of the present application, the first image analysis algorithm may be a first landmark detection algorithm, a target eye disease may be thyroid eye disease, the diagnosis object DO may be the eyes, and the first photographing parameter may be landmarks of the eyes. Regarding the first photographing parameter, the landmarks of the eyes may be selected among landmarks of the face obtained through the first landmark detection algorithm, or only the landmarks of the eyes may be obtained through the first landmark algorithm (see FIG. 15A). According to an embodiment of the present application, the first photographing parameter may be a pupil position based on a pupil landmark and/or an iris landmark, when the first landmark detection algorithm detects the pupil landmark and/or the iris landmark. According to other embodiment of the present application, the first photographing parameter may be a range of possible position of a pupil based on an eyeball-eyelid boundary, when the first landmark detection algorithm detects the eyeball-eyelid boundary.

The second image analysis algorithm may be a second landmark detection algorithm, a target eye disease may be thyroid eye disease, the diagnosis object DO may be the eyes, and the first verification parameter may be landmarks of the eyes. Similarly, regarding the first verification parameter, the landmarks of the eyes may be selected among landmarks of the face obtained through the second landmark detection algorithm, or only the landmarks of the eyes may be obtained through the second landmark algorithm. According to an embodiment of the present application, the first verification parameter may be a pupil position based on a pupil landmark and/or an iris landmark, when the second landmark detection algorithm detects the pupil landmark and/or the iris landmark. According to other embodiment of the present application, the first verification parameter may be a range of possible position of a pupil based on an eyeball-eyelid boundary, when the second landmark detection algorithm detects the eyeball-eyelid boundary.

Herein, according to an embodiment of the present application, the first photographing condition may be set to be a condition in which i) the landmarks of the eyes obtained through the first landmark detection algorithm and ii) pre-stored eye areas are different from each other by a threshold value or less. According to other embodiment of the present application, the first photographing condition may be set to be a condition in which i) the pupil position and/or the range of possible position of the pupil obtained through the first landmark detection algorithm and ii) pre-stored pupil position and/or range of possible position of the pupil are different from each other by a threshold value or less.

Herein, according to an embodiment of the present application, the first verification condition may be set to be a condition in which i) the landmarks of the eyes obtained through the first landmark detection algorithm and ii) the landmarks of the eyes obtained through the second landmark detection algorithm are different from each other by a threshold value or less. According to other embodiment of the present application, the first verification condition may be set to be a condition in which i) the pupil position and/or the range of possible position of the pupil obtained through the first landmark detection algorithm and ii) the pupil position and/or the range of possible position of the pupil obtained through the second landmark detection algorithm are different from each other by a threshold value or less.

According to another embodiment of the present application, the first image analysis algorithm may be the first landmark detection algorithm, a target eye disease may be thyroid eye disease, the diagnosis object DO may be the eyes, and the first photographing parameter may be landmarks of the eyes. Regarding the first photographing parameter, the landmarks of the eyes may be selected among landmarks of the face obtained through the first landmark detection algorithm, or only the landmarks of the eyes may be obtained through the first landmark algorithm (see FIG. 15A). According to an embodiment of the present application, the first photographing parameter may be a pupil position based on a pupil landmark and/or an iris landmark, when the first landmark detection algorithm detects the pupil landmark and/or iris landmark. According to other embodiment of the present application, the first photographing parameter may be a range of possible position of a pupil based on an eyeball-eyelid boundary, when the first landmark detection algorithm detects the eyeball-eyelid boundary.

The second image analysis algorithm may be an image segmentation algorithm, a target eye disease may be thyroid eye disease, the diagnosis object DO may be the eyes, and the first verification parameter may be iris areas predicted using the image segmentation algorithm (see FIG. 15B). According to an embodiment of the present application, the first verification parameter may be a range of possible position of a pupil based on an inner area of an eyeball-eyelid boundary (ie, an eyeball area), when the image segmentation algorithm predicts the eyeball area. According to other embodiment of the present application, the first verification parameter may be a pupil position based on an inner area of corneal boundary (ie, a corneal area), when the image segmentation algorithm predicts the corneal area.

Herein, according to an embodiment of the present application, the first photographing condition may be set to be a condition in which i) the landmarks of the eyes obtained through the first landmark detection algorithm and ii) pre-stored eye areas are different from each other by a threshold value or less. According to other embodiment of the present application, the first photographing condition may be set to be a condition in which i) the pupil position and/or the range of possible position of the pupil obtained through the first landmark detection algorithm and ii) pre-stored pupil position and/or range of possible position of the pupil are different from each other by a threshold value or less.

Herein, according to an embodiment of the present application, the first verification condition may be set to be a condition in which the centers of iris areas predicted using the image segmentation algorithm are included inside the landmarks of the eyes obtained through the first landmark detection algorithm. According to other embodiment of the present application, the first verification condition may be set to be a condition in which i) the pupil position and/or the range of possible position of the pupil obtained through the first landmark detection algorithm and ii) the pupil position and/or the range of possible position of the pupil obtained through the image segmentation algorithm are different from each other by a threshold value or less.

According to an embodiment of the present application, a diagnostic module for obtaining diagnosis assistance information on the basis of a diagnostic image may be trained using images verified through the above-described procedure. In other words, even in training the diagnostic module, an image is obtained through the above-described image verification method and the diagnostic module is trained using data with more consistency, thereby improving accuracy.

Figure 16A:
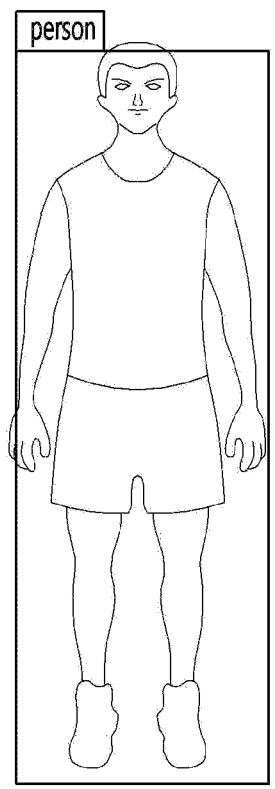
FIGS. 16A and 16B are diagrams illustrating a method of acquiring a body imbalance-related image according to an embodiment of the present application.
Figure 16B:
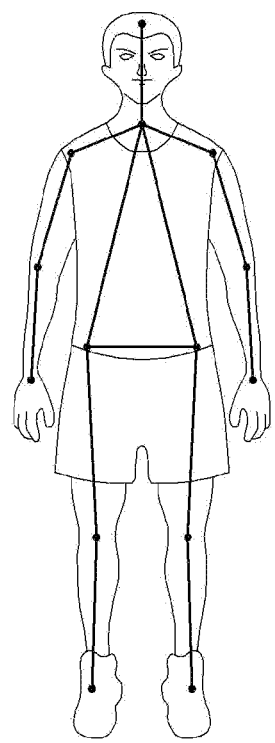

FIGS. 16A and 16B are diagrams illustrating a method of acquiring a body imbalance-related image according to an embodiment of the present application.

According to an embodiment of the present application, the first image analysis algorithm may be an object detection algorithm, the target disease may be body imbalance, the diagnosis object DO may be the entire body, and the first photographing parameter may be a bounding box corresponding to the entire body (see FIG. 16A). The second image analysis algorithm may be an object detection algorithm, the target disease may be body imbalance, the diagnosis object DO may be the entire body, and the first verification parameter may be a bounding box corresponding to the entire body.

Herein, the first photographing condition may be set to be a condition in which i) the bounding box obtained through the first image analysis algorithm and ii) a pre-stored entire body area are different from each other by a threshold value or less.

Herein, the first verification condition may be set to be a condition in which i) the bounding box obtained through the second image analysis algorithm and ii) the bounding box obtained through the first image analysis algorithm are different from each other by a threshold value or less.

According to another embodiment of the present application, the first image analysis algorithm may be an object detection algorithm, the target disease may be body imbalance, the diagnosis object DO may be the entire body, and the first photographing parameter may be a bounding box corresponding to the entire body (see FIG. 16A). The second image analysis algorithm may be a pose detection algorithm, the target disease may be body imbalance, the diagnosis object DO may be the entire body, and the first verification parameter may be lines corresponding to the joints.

Herein, the first photographing condition may be set to be a condition in which i) the bounding box obtained through the first image analysis algorithm and ii) a pre-stored entire body area are different from each other by a threshold value or less.

Herein, the first verification condition may be set to be a condition in which the lines corresponding to the joints obtained through the second image analysis algorithm are inside the bounding box obtained through the first image analysis algorithm.

Although not shown separately, without being limited to the above description, the following form may be realized: the user terminal 1000 and the server 2000 may determine whether feature points of the face are detected for stroke diagnosis, or the user terminal 1000 may determine whether the feature points of the face are detected, and the server 2000 may determine the aspect ratio of a specific part on the basis of the feature points of the face. However, no limitation thereto is imposed.

In addition, describing the concept of the present specification, it has been described that the user terminal 1000 performs image photographing and the server 2000 performs image verification, but this is merely one case for convenience of description. The following form may be realized:

the user terminal 1000 may perform all the operations described in the present specification; or the user terminal 1000 perform only image acquisition and storage and the server 2000 determines whether the photographing parameters satisfy the criteria and the verification parameters satisfy the criteria. However, no limitation thereto is imposed.

In addition, describing the concept of the present specification, the above description is given assuming that the photographing device 1000 is a user terminal, but this is merely one case for convenience of description. The photographing device 1000 may be a user terminal for taking images, a user terminal for taking fundus images or X-ray images, or a medical device rather than a user terminal.

The methods according to the above-described embodiments may be written as computer-executable programs, and may be implemented in a general-use digital computer that executes the programs by using a computer-readable recording medium. In addition, data structures, program instructions, or data files, which may be used in the embodiments of the present disclosure, may be recorded on a computer-readable recording medium through various means. Examples of the computer-readable recording medium may include all types of storage devices in which data readable by a computer system is stored. Examples of the computer-readable recording medium include: magnetic media such as hard disks, floppy disks, and magnetic tapes; optical media such as CD-ROMs and DVDs; magneto-optical media such as floptical disks; and hardware devices, such as ROM, RAM, flash memory, etc., which are particularly configured to store and implement program instructions. In addition, the computer-readable recording medium may be a transmission medium for transmitting signals designating program instructions, data structures, etc. Examples of the program instructions include machine language codes, such as ones generated by a compiler, and high-level language codes executable by a computer using an interpreter, etc.

Although the embodiments of the present application have been described with reference to the limited embodiments and drawings, the technical idea or embodiments disclosed in the present specification are not limited to the above-described embodiments, and it will be understood by those skilled in the art that various modifications and variations may be made from the description. Therefore, the scope of the present application is defined not by the description above but by the following claims, and all their equivalents will fall within the scope and spirit of the present disclosure.

MODE FOR INVENTION

-

What is claimed is:

1. A diagnostic system, comprising: a user terminal configured to take an image; and a server configured to obtain diagnosis assistance information on the basis of the image,
wherein the user terminal is configured to:
obtain a first photographing parameter including information related to at least one of (1) a first detected position of a diagnosis object or (2) whether the diagnosis object is detected or not by analyzing a first image with a first image analysis algorithm,
determine whether a pre-stored condition is satisfied, wherein the pre-stored condition requires that the first photographing parameter satisfy a first condition,
store the first photographing parameter and a captured image in response to determining that the pre-stored condition is satisfied, and
transmit the first photographing parameter and the captured image to the server in response to determining that the pre-stored condition is satisfied,
the server is configured to:
receive the first photographing parameter and the captured image from the user terminal,
obtain a first verification parameter including information related to at least one of (1) a second detected position of the diagnosis object or (2) whether the diagnosis object is detected or not by analyzing the captured image with a second image analysis algorithm,
determine a difference between the first verification parameter and the first photographing parameter by comparing the first verification parameter with the first photographing parameter;
determine to use the captured image as a diagnostic image in response to determining that the difference is less than or equal to a threshold value, and
obtain the diagnosis assistance information by using the diagnostic image,
the first image analysis algorithm and the second image analysis algorithm are different algorithms, and
the diagnosis object is a body part associated with a target disease for which the diagnosis assistance information is obtained.

2. The diagnostic system of claim 1, wherein the first photographing parameter includes information on the first detected position of the diagnosis object in the first image, and
the user terminal is configured to determine whether the pre-stored condition is satisfied by comparing the first photographing parameter with a pre-stored diagnosis object area.

3. The diagnostic system of claim 2, wherein the first image analysis algorithm is a first landmark detection algorithm, and
the target disease is thyroid eye disease, the diagnosis object is an eye, and the first photographing parameter is a first landmark of the eye.

4. The diagnostic system of claim 2, wherein the second image analysis algorithm is a second landmark detection algorithm,
the target disease is thyroid eye disease,
the diagnosis object is an eye, and
the first verification parameter is a second landmark of the eye and includes information on the second detected position of the diagnosis object in the captured image.

5. The diagnostic system of claim 2, wherein the second image analysis algorithm is an image segmentation algorithm,
the target disease is thyroid eye disease,
the diagnosis object is an eye, and
the first verification parameter is an iris area and includes information on the second detected position of the diagnosis object in the captured image.

6. The diagnostic system of claim 1,
wherein the user terminal is configured to obtain the images according to a preset frame rate, analyze at least a part of the obtained images with the first image analysis algorithm, store one of the obtained images as the captured image, and transmit the captured image to the server.

7. The diagnostic system of claim 1, wherein the user terminal is configured to, in response to determining that the first photographing parameter for the first image does not satisfy the first condition, analyze a second image with the first image analysis algorithm,
wherein the second image is obtained after it is determined that the first photographing parameter for the first image does not satisfy the first condition.

8. The diagnostic system of claim 1, wherein the user terminal is configured to,
in response to determining that the first photographing parameter for the first image satisfies the first condition, store a second image as the captured image,
wherein the second image is obtained after it is determined that the first photographing parameter for the first image satisfies the first condition.

9. The diagnostic system of claim 1, wherein the first image analysis algorithm has a smaller amount of operation than the second image analysis algorithm to have an advantage of real-time processing.

10. The diagnostic system of claim 1, wherein the user terminal is configured to obtain a second photographing parameter for the first image,
wherein the pre-stored condition further requires that the second photographing parameter satisfy a second condition.

11. The diagnostic system of claim 10, wherein in the user terminal, a period of obtaining the first photographing parameter and a period of obtaining the second photographing parameter are different from each other.

12. The diagnostic system of claim 1, wherein the user terminal is configured to obtain a second to an N-th photographing parameter for the first image,
wherein the pre-stored condition further requires that at least some of the second to the N-th photographing parameter satisfy a corresponding second to an N-th condition, respectively,
wherein the N is a natural number equal to or greater than 2.

13. The diagnostic system of claim 12, wherein the server is configured to obtain a second to an M-th verification parameter for the captured image, and
determine to use the captured image as the diagnostic image in response to determining that the difference is less than or equal to the threshold value and at least some of the second to the M-th verification parameter are satisfied,
wherein the M is a natural number equal to or greater than 2.

14. The diagnostic system of claim 1, wherein the server is configured to obtain the diagnosis assistance information by using the diagnostic image and a diagnostic model, and
the diagnostic model is trained using images including the diagnosis object, and information on whether the target disease has occurred.

15. A diagnostic image verification method, comprising:
obtaining a first image;
obtaining a first photographing parameter including information related to at least one of (1) a first detected position of a diagnosis object or (2) whether the diagnosis object is detected or not by analyzing the first image with a first image analysis algorithm;
determining whether a pre-stored condition is satisfied, wherein the pre-stored condition requires that the first photographing parameter satisfy a first condition;
storing the first photographing parameter and a captured image in response to determining that the pre-stored condition is satisfied;
obtaining a first verification parameter including information related to at least one of (1) a second detected position of the diagnosis object or (2) whether the diagnosis object is detected or not by analyzing the captured image with a second image analysis algorithm;
determining a difference between the first verification parameter and the first photographing parameter by comparing the first verification parameter with the first photograph parameter;
determining to use the captured image as a diagnostic image in response to determining that the difference is less than or equal to a threshold value; and
obtaining diagnosis assistance information by using the diagnostic image,
wherein the first image analysis algorithm and the second image analysis algorithm are different algorithms, and
the diagnosis object is a body part associated with a target disease for which the diagnosis assistance information is obtained.

16. The diagnostic image verification method of claim 15, wherein the first image analysis algorithm is a first landmark detection algorithm,
the target disease is thyroid eye disease,
the diagnosis object is an eye,
the first photographing parameter is a landmark of the eye and includes information on the first detected position of the diagnosis object in the first image, and
the determining whether the pre-stored condition is satisfied includes comparing the first photographing parameter with a pre-stored diagnosis object area.

17. The diagnostic image verification method of claim 15, wherein the first photographing parameter includes information on the first detected position of the diagnosis object in the first image,
the determining whether the pre-stored condition is satisfied includes comparing the first photographing parameter with a pre-stored diagnosis object area,
the second image analysis algorithm is a second landmark detection algorithm,
the target disease is thyroid eye disease,
the diagnosis object is an eye, and
the first verification parameter is a landmark of the eye and includes information on the second detected position of the diagnosis object in the captured image.

18. The diagnostic image verification method of claim 15, wherein the first photographing parameter includes information on the first detected position of the diagnosis object in the first image,
the determining whether the pre-stored condition is satisfied includes comparing the first photographing parameter with a pre-stored diagnosis object area,
the second image analysis algorithm is an image segmentation algorithm,
the target disease is thyroid eye disease,
the diagnosis object is an eye, and
the first verification parameter is an iris area and includes information on the second detected position of the diagnosis object in the captured image.

19. The diagnostic image verification method of claim 15, wherein the first image analysis algorithm has a smaller amount of operation than the second image analysis algorithm to have an advantage of real-time processing.

20. A non-transitory computer-readable recording medium having a program recorded thereon, the program for performing the method of claim 15.

* * * * *